(12) United States Patent
Richards et al.

(10) Patent No.: US 8,584,279 B2
(45) Date of Patent: Nov. 19, 2013

(54) PULMONARY MATTRESS

(75) Inventors: Sandy M. Richards, Pershing, IN (US);
Christopher R. O'Keefe, Batesville, IN (US); Bradley T. Wilson, Tyler, TX (US); Kenith W. Chambers, Batesville, IN (US); Mayur Yermaneni, Shrewsbury, MA (US); Gregory W. Branson, Batesville, IN (US); Michael Z Sleva, Atlanta, GA (US); Karen M. Gove, Maple Grove, MN (US); Andrew F. Skinner, Batesville, IN (US); Stephen R. Schulte, Gibsonia, PA (US); Todd P. O'Neal, Fairfield, OH (US); Rachel Hopkins King, Harrison, OH (US); Teresa M. Mirabella, Daniel Island, SC (US); Paula M. Cooper, Mt. Pleasat, SC (US); Eric R. Meyer, Greensburg, IN (US)

(73) Assignee: Hill-Rom Services, Inc., Batesviille, IN (US)

( * ) Notice: Subject to any disclaimer, the term of this patent is extended or adjusted under 35 U.S.C. 154(b) by 0 days.

(21) Appl. No.: 13/243,483

(22) Filed: Sep. 23, 2011

(65) Prior Publication Data
US 2012/0016281 A1    Jan. 19, 2012

Related U.S. Application Data

(63) Continuation of application No. 12/122,808, filed on May 19, 2008, now Pat. No. 8,108,957.

(60) Provisional application No. 60/941,092, filed on May 31, 2007.

(51) Int. Cl.
*A47B 71/00*  (2006.01)

(52) U.S. Cl.
USPC .............................................. 5/600; 601/150

(58) Field of Classification Search
USPC ............... 5/600, 715, 658, 503.1, 655.3, 713; 601/41, 148–152
See application file for complete search history.

(56) References Cited

U.S. PATENT DOCUMENTS

| | | | |
|---|---|---|---|
| 1,772,310 | A | 8/1930 | Hart |
| 3,065,344 | A | 11/1962 | Chervenka |
| 3,462,778 | A | 8/1969 | Whitney |
| 3,492,988 | A | 2/1970 | De Mare |

(Continued)

FOREIGN PATENT DOCUMENTS

| | | |
|---|---|---|
| WO | 8801158 A1 | 2/1988 |
| WO | 2004082551 A | 9/2004 |
| WO | WO 2004/082551 | 9/2004 |

OTHER PUBLICATIONS

Partial European Search Report for EP Application No. 08251896 completed Apr. 14, 2009.

(Continued)

*Primary Examiner* — Nicholas Polito
(74) *Attorney, Agent, or Firm* — Barnes & Thornburg LLP

(57) ABSTRACT

A patient support surface including a cover defining an interior region, a layer of three dimensional material, located at the interior region, and an air circulation device disposed adjacent the layer of three dimensional material. The patient support surface includes at least one of a percussion device and a vibration device, located at the interior region.

14 Claims, 23 Drawing Sheets

(56) References Cited

U.S. PATENT DOCUMENTS

| | | |
|---|---|---|
| 3,939,829 A | 2/1976 | Spann |
| 4,068,870 A | 1/1978 | Whitney et al. |
| 4,108,170 A | 8/1978 | Spann |
| 4,149,541 A | 4/1979 | Gammons et al. |
| 4,233,700 A | 11/1980 | Spann |
| 4,453,538 A | 6/1984 | Whitney |
| 4,471,952 A | 9/1984 | Spann |
| 4,542,547 A | 9/1985 | Sato |
| 4,573,456 A | 3/1986 | Spann |
| 4,597,384 A | 7/1986 | Whitney |
| 4,603,445 A | 8/1986 | Spann |
| 4,638,519 A | 1/1987 | Hess |
| 4,665,574 A | 5/1987 | Filips et al. |
| 4,686,725 A | 8/1987 | Mitchell |
| 4,700,447 A | 10/1987 | Spann |
| 4,722,332 A | 2/1988 | Saggers |
| 4,729,598 A | 3/1988 | Hess |
| 4,768,241 A | 9/1988 | Beney |
| 4,793,328 A | 12/1988 | Kolstedt et al. |
| 4,797,962 A | 1/1989 | Goode |
| 4,839,932 A | 6/1989 | Williamson |
| 4,858,596 A | 8/1989 | Kolstedt et al. |
| 4,860,397 A | 8/1989 | Gusakov |
| 4,862,538 A | 9/1989 | Spann et al. |
| 4,866,800 A | 9/1989 | Bedford |
| 4,888,958 A | 12/1989 | Ella |
| 4,896,389 A | 1/1990 | Chamberland |
| 4,901,387 A | 2/1990 | Luke |
| 4,905,266 A | 2/1990 | Kuck et al. |
| 4,907,308 A | 3/1990 | Leininger et al. |
| 4,914,771 A | 4/1990 | Afeyan |
| D307,687 S | 5/1990 | Raburn |
| D307,688 S | 5/1990 | Schaefer |
| D307,689 S | 5/1990 | Schaefer |
| D307,690 S | 5/1990 | Raburn |
| 4,934,002 A | 6/1990 | Watanabe |
| 4,938,208 A | 7/1990 | Dye |
| 4,941,221 A | 7/1990 | Kanzer |
| 4,944,060 A | 7/1990 | Perry et al. |
| 4,945,588 A | 8/1990 | Cassidy et al. |
| 4,949,412 A | 8/1990 | Goode |
| 4,949,413 A | 8/1990 | Goodwin |
| 4,949,414 A | 8/1990 | Thomas et al. |
| 4,951,334 A | 8/1990 | Maier |
| 4,971,044 A | 11/1990 | Dye |
| D315,406 S | 3/1991 | Dye |
| 5,003,654 A | 4/1991 | Vrzalik |
| 5,005,240 A | 4/1991 | Vrzalik |
| 5,007,124 A | 4/1991 | Raburn et al. |
| 5,010,610 A | 4/1991 | Ackley |
| 5,016,268 A | 5/1991 | Lotman |
| 5,022,110 A | 6/1991 | Stroh |
| 5,025,519 A | 6/1991 | Spann et al. |
| 5,035,014 A | 7/1991 | Blanchard |
| 5,035,016 A | 7/1991 | Mori et al. |
| 5,039,158 A | 8/1991 | Maier |
| 5,044,029 A | 9/1991 | Vrzalik |
| 5,052,067 A | 10/1991 | Thomas et al. |
| 5,062,167 A | 11/1991 | Thomas et al. |
| 5,073,999 A | 12/1991 | Thomas et al. |
| D322,907 S | 1/1992 | Raburn |
| 5,090,077 A | 2/1992 | Caden et al. |
| 5,095,568 A | 3/1992 | Thomas et al. |
| 5,109,165 A | 4/1992 | Gusakov |
| D326,976 S | 6/1992 | Wickis, Jr. et al. |
| 5,121,513 A | 6/1992 | Thomas et al. |
| D327,738 S | 7/1992 | Dye |
| D328,346 S | 7/1992 | Dye |
| 5,140,309 A | 8/1992 | Gusakov |
| 5,142,719 A | 9/1992 | Vrzalik |
| D330,250 S | 10/1992 | Dye |
| D330,251 S | 10/1992 | Dye |
| 5,152,021 A | 10/1992 | Vrzalik |
| 5,168,589 A | 12/1992 | Stroh et al. |
| 5,179,742 A | 1/1993 | Oberle |
| 5,183,039 A | 2/1993 | Sarian et al. |
| 5,184,112 A | 2/1993 | Gusakov |
| D336,400 S | 6/1993 | Mitchell et al. |
| 5,249,318 A | 10/1993 | Loadsman |
| 5,251,347 A | 10/1993 | Hopper et al. |
| 5,252,278 A | 10/1993 | Spann et al. |
| 5,255,404 A | 10/1993 | Dinsmoor, III et al. |
| 5,267,364 A | 12/1993 | Volk |
| 5,272,778 A | 12/1993 | Gore |
| 5,301,457 A | 4/1994 | Seely |
| 5,303,436 A | 4/1994 | Dinsmoor, III et al. |
| 5,305,483 A | 4/1994 | Watkins |
| 5,325,551 A | 7/1994 | Tappel et al. |
| 5,383,894 A | 1/1995 | Dye |
| D355,322 S | 2/1995 | Ackley et al. |
| D355,488 S | 2/1995 | Hargest et al. |
| 5,396,671 A | 3/1995 | Stacy |
| D357,736 S | 4/1995 | Dye |
| D357,740 S | 4/1995 | Kennemore |
| 5,412,821 A | 5/1995 | Wilkinson |
| D362,721 S | 9/1995 | Peeler et al. |
| 5,459,896 A | 10/1995 | Raburn et al. |
| D363,988 S | 11/1995 | Dye |
| D364,459 S | 11/1995 | Dye |
| D364,460 S | 11/1995 | Dye |
| D364,680 S | 11/1995 | Dye |
| 5,483,709 A | 1/1996 | Foster et al. |
| 5,487,196 A | 1/1996 | Wilkinson et al. |
| 5,493,742 A | 2/1996 | Klearman |
| 5,509,155 A | 4/1996 | Zigarac et al. |
| 5,509,160 A | 4/1996 | Schubert |
| 5,511,260 A | 4/1996 | Dinsmoor, III et al. |
| D369,664 S | 5/1996 | Dye |
| 5,513,406 A | 5/1996 | Foster et al. |
| D373,192 S | 8/1996 | Murphy et al. |
| 5,542,136 A | 8/1996 | Tappel |
| 5,542,138 A | 8/1996 | Williams et al. |
| D374,368 S | 10/1996 | Sprigle et al. |
| D374,931 S | 10/1996 | Cesaroni et al. |
| 5,560,057 A | 10/1996 | Madsen et al. |
| 5,568,660 A | 10/1996 | Raburn et al. |
| D376,013 S | 11/1996 | Sandman et al. |
| 5,586,346 A | 12/1996 | Stacy et al. |
| 5,588,954 A | 12/1996 | Ribando et al. |
| 5,594,963 A | 1/1997 | Berkowitz |
| 5,603,133 A | 2/1997 | Vrzalik |
| 5,606,754 A | 3/1997 | Hand et al. |
| 5,611,096 A | 3/1997 | Bartlett et al. |
| 5,611,772 A | 3/1997 | Fujimoto et al. |
| 5,630,238 A | 5/1997 | Weismiller et al. |
| 5,649,331 A | 7/1997 | Wilkinson et al. |
| 5,652,985 A | 8/1997 | Wilkinson et al. |
| 5,664,270 A | 9/1997 | Bell et al. |
| 5,674,262 A | 10/1997 | Tumey |
| 5,676,639 A | 10/1997 | Schild |
| 5,699,570 A | 12/1997 | Wilkinson et al. |
| 5,704,084 A | 1/1998 | Evans et al. |
| D390,665 S | 2/1998 | Kennemore |
| D393,071 S | 3/1998 | Kennemore |
| 5,725,485 A | 3/1998 | Ribando et al. |
| 5,729,853 A | 3/1998 | Thompson |
| 5,731,062 A | 3/1998 | Kim et al. |
| 5,737,788 A | 4/1998 | Castellino et al. |
| 5,745,939 A | 5/1998 | Flick et al. |
| 5,755,000 A | 5/1998 | Thompson |
| 5,769,797 A | 6/1998 | Van Brunt et al. |
| 5,771,511 A | 6/1998 | Kummer et al. |
| 5,787,531 A | 8/1998 | Pepe |
| 5,787,534 A | 8/1998 | Hargest et al. |
| 5,794,288 A | 8/1998 | Soltani et al. |
| 5,794,289 A | 8/1998 | Wortman et al. |
| 5,795,312 A | 8/1998 | Dye |
| 5,797,155 A | 8/1998 | Maier et al. |
| 5,815,864 A | 10/1998 | Sloop |
| 5,817,069 A | 10/1998 | Arnett |
| 5,869,164 A | 2/1999 | Nickerson et al. |
| 5,882,349 A | 3/1999 | Wilkerson et al. |
| 5,890,245 A | 4/1999 | Klearman et al. |
| 5,901,393 A | 5/1999 | Pepe et al. |

(56) References Cited

U.S. PATENT DOCUMENTS

| | | |
|---|---|---|
| 5,913,774 A | 6/1999 | Feddema |
| 5,926,883 A | 7/1999 | Rechin et al. |
| 5,926,884 A | 7/1999 | Biggie et al. |
| 5,951,502 A | 9/1999 | Peeler et al. |
| 5,960,497 A | 10/1999 | Castellino et al. |
| 5,963,137 A | 10/1999 | Waters, Sr. |
| 5,970,550 A | 10/1999 | Gazes |
| 5,983,429 A | 11/1999 | Stacy et al. |
| 5,987,668 A | 11/1999 | Ackley |
| 6,012,186 A | 1/2000 | Soltani et al. |
| 6,014,346 A | 1/2000 | Malone |
| 6,025,782 A | 2/2000 | Newham |
| 6,030,353 A | 2/2000 | Van Brunt |
| 6,036,271 A | 3/2000 | Wilkinson et al. |
| 6,036,662 A | 3/2000 | Van Brunt et al. |
| 6,047,424 A | 4/2000 | Osborne et al. |
| 6,073,291 A | 6/2000 | Davis |
| 6,079,070 A | 6/2000 | Flick |
| 6,085,372 A | 7/2000 | James et al. |
| 6,099,951 A | 8/2000 | Flick et al. |
| 6,115,860 A | 9/2000 | Vrzalik |
| 6,131,469 A | 10/2000 | Wortman et al. |
| 6,133,837 A | 10/2000 | Riley |
| 6,145,142 A | 11/2000 | Rechin et al. |
| 6,145,143 A | 11/2000 | Hicks et al. |
| 6,148,461 A | 11/2000 | Cook et al. |
| 6,152,169 A | 11/2000 | Flick |
| 6,155,996 A | 12/2000 | Van Brunt et al. |
| 6,163,908 A | 12/2000 | Vrzalik |
| 6,208,250 B1 | 3/2001 | Dixon et al. |
| 6,210,345 B1 | 4/2001 | Van Brunt |
| 6,212,718 B1 | 4/2001 | Stolpmann et al. |
| 6,223,369 B1 | 5/2001 | Maier et al. |
| 6,230,342 B1 | 5/2001 | Haugs |
| 6,256,819 B1 | 7/2001 | Maier et al. |
| 6,256,822 B1 | 7/2001 | Weston et al. |
| D446,791 S | 8/2001 | Beckham |
| 6,269,504 B1 | 8/2001 | Romano et al. |
| 6,269,505 B1 | 8/2001 | Wilkinson |
| 6,279,183 B1 | 8/2001 | Kummer et al. |
| 6,282,736 B1 | 9/2001 | Hand et al. |
| 6,282,737 B1 | 9/2001 | Vrzalik |
| 6,296,617 B1 | 10/2001 | Peeler et al. |
| 6,317,912 B1 | 11/2001 | Graebe et al. |
| 6,320,510 B2 | 11/2001 | Menkedick et al. |
| 6,336,237 B1 | 1/2002 | Schmid |
| 6,340,025 B1 | 1/2002 | Van Brunt |
| 6,341,398 B1 | 1/2002 | Heimbrock et al. |
| D453,560 S | 2/2002 | Van Brunt |
| 6,353,950 B1 | 3/2002 | Bartlett et al. |
| 6,370,716 B1 | 4/2002 | Wilkinson |
| 6,379,316 B1 | 4/2002 | Van Brunt et al. |
| 6,415,791 B1 | 7/2002 | Van Brunt |
| 6,421,859 B1 | 7/2002 | Hicks et al. |
| 6,438,776 B2 | 8/2002 | Ferrand et al. |
| 6,441,742 B1 | 8/2002 | Lovely et al. |
| 6,442,780 B1 | 9/2002 | Phillips et al. |
| 6,447,467 B1 | 9/2002 | Barak |
| 6,471,663 B1 | 10/2002 | Van Brunt et al. |
| 6,487,739 B1 | 12/2002 | Harker |
| 6,488,043 B2 | 12/2002 | Flick |
| 6,493,568 B1 | 12/2002 | Bell et al. |
| 6,494,852 B1 | 12/2002 | Barak et al. |
| 6,517,510 B1 | 2/2003 | Stewart et al. |
| 6,536,056 B1 | 3/2003 | Vrzalik et al. |
| 6,544,200 B1 | 4/2003 | Smith et al. |
| 6,560,804 B2 | 5/2003 | Wise et al. |
| 6,566,833 B2 | 5/2003 | Bartlett |
| 6,578,219 B1 | 6/2003 | Gabel et al. |
| 6,583,727 B2 | 6/2003 | Nunome |
| 6,591,437 B1 | 7/2003 | Phillips |
| 6,606,754 B1 | 8/2003 | Flick |
| 6,610,021 B1 | 8/2003 | Bock |
| 6,611,783 B2 | 8/2003 | Kelly, Jr. et al. |
| 6,646,556 B1 | 11/2003 | Smith et al. |
| 6,652,140 B1 | 11/2003 | Taber et al. |
| 6,662,391 B2 | 12/2003 | Wilson et al. |
| 6,687,937 B2 | 2/2004 | Harker |
| 6,689,079 B2 | 2/2004 | Flick et al. |
| 6,691,347 B2 | 2/2004 | Hand et al. |
| 6,694,557 B1 | 2/2004 | Bobey et al. |
| 6,695,798 B2 | 2/2004 | Chang |
| 6,698,046 B1 | 3/2004 | Wu |
| 6,701,556 B2 | 3/2004 | Romano et al. |
| 6,708,352 B2 | 3/2004 | Salvatini et al. |
| 6,721,979 B1 | 4/2004 | Vrzalik et al. |
| 6,730,115 B1 | 5/2004 | Heaton |
| 6,736,785 B1 | 5/2004 | Van Brunt |
| 6,739,001 B2 | 5/2004 | Flick et al. |
| 6,745,996 B1 | 6/2004 | Guthrie |
| 6,764,455 B2 | 7/2004 | Van Brunt et al. |
| 6,782,574 B2 | 8/2004 | Totton et al. |
| 6,784,797 B2 | 8/2004 | Smith et al. |
| 6,786,879 B1 * | 9/2004 | Bolam et al. .................. 601/152 |
| 6,791,460 B2 | 9/2004 | Dixon et al. |
| 6,813,790 B2 | 11/2004 | Flick et al. |
| 6,817,363 B2 * | 11/2004 | Biondo et al. ................. 128/845 |
| 6,820,640 B2 | 11/2004 | Hand et al. |
| 6,821,258 B2 | 11/2004 | Reed et al. |
| 6,822,571 B2 | 11/2004 | Conway |
| 6,826,795 B2 | 12/2004 | Wilkinson |
| 6,855,158 B2 | 2/2005 | Stolpmann |
| D502,350 S | 3/2005 | O'Reagan |
| 6,859,967 B2 | 3/2005 | Harrison et al. |
| 6,871,365 B2 | 3/2005 | Flick et al. |
| 6,874,185 B1 | 4/2005 | Phillips et al. |
| 6,892,405 B1 | 5/2005 | Dimitriu et al. |
| 6,901,216 B2 | 5/2005 | Jusiak et al. |
| 6,907,633 B2 | 6/2005 | Paolini et al. |
| 6,928,681 B1 | 8/2005 | Stacy |
| 6,934,361 B2 | 8/2005 | Ohkoda |
| 6,942,687 B1 | 9/2005 | Heaton et al. |
| 6,943,694 B1 | 9/2005 | Ellis |
| 7,030,764 B2 | 4/2006 | Smith et al. |
| 7,036,171 B2 | 5/2006 | Wu |
| 7,065,815 B2 | 6/2006 | Buchanan |
| 7,092,376 B2 | 8/2006 | Schuman |
| 7,152,264 B2 | 12/2006 | Boyd |
| 7,171,711 B2 | 2/2007 | Gowda |
| 7,240,386 B1 | 7/2007 | McKay et al. |
| 7,296,315 B2 | 11/2007 | Totton et al. |
| 7,319,386 B2 * | 1/2008 | Collins et al. ............ 340/539.12 |
| 7,487,562 B2 | 2/2009 | Frondorf et al. |
| 7,641,623 B2 * | 1/2010 | Biondo et al. ................. 601/149 |
| 2002/0067273 A1 | 6/2002 | Jaques et al. |
| 2002/0070867 A1 | 6/2002 | Conway et al. |
| 2003/0208849 A1 | 11/2003 | Wilkinson |
| 2003/0236474 A1 | 12/2003 | Singh |
| 2004/0031103 A1 | 2/2004 | Wyatt et al. |
| 2004/0068801 A1 | 4/2004 | Wilkinson |
| 2004/0100376 A1 | 5/2004 | Lye et al. |
| 2004/0177450 A1 | 9/2004 | Salvatini et al. |
| 2004/0237203 A1 | 12/2004 | Romano et al. |
| 2004/0256588 A1 | 12/2004 | Guthrie |
| 2005/0076448 A1 | 4/2005 | O'Reagan |
| 2005/0081300 A1 | 4/2005 | O'Reagan et al. |
| 2005/0177952 A1 | 8/2005 | Wilkinson et al. |
| 2006/0075559 A1 | 4/2006 | Skinner et al. |
| 2006/0112489 A1 | 6/2006 | Bobey et al. |
| 2006/0156473 A1 | 7/2006 | Chambers et al. |
| 2007/0101506 A1 | 5/2007 | Pirzada |
| 2007/0234482 A1 | 10/2007 | Wright |
| 2007/0235036 A1 | 10/2007 | Bobey et al. |
| 2009/0013470 A1 | 1/2009 | Richards et al. |

OTHER PUBLICATIONS

European Official Action from EP 08 251 896.0-1257 dated Aug. 25, 2011, 5 pages.
European Search Report for Application No. 12159618.3-1257, dated Aug. 31, 2012, 6 pages.
US 5,152,022, 10/1992, Vrzalik (withdrawn)

* cited by examiner

PULMONARY MATTRESS

CROSS-REFERENCE TO RELATED APPLICATIONS

This application is a continuation of U.S. patent application Ser. No. 12/122,808, filed May 19, 2008, now U.S. Pat. No. 8,108,957, which claims the benefit of U.S. Provisional Patent Application Ser. No. 60/941,092, filed May 31, 2007; both of which are incorporated herein by this reference in their entirety.

The present application is also related to U.S. patent application Ser. No. 11/119,980, now abandoned, entitled PRESSURE RELIEF SURFACE, and U.S. patent application Ser. No. 11/119,991, now U.S. Pat. No. 7,883,478, entitled PATIENT SUPPORT HAVING REAL TIME PRESSURE CONTROL, and U.S. patent application Ser. No. 11/119,635, now U.S. Pat. No. 7,557,718, entitled LACK OF PATIENT MOVEMENT MONITOR AND METHOD, and U.S. patent application Ser. No. 11/120,080, now abandoned, entitled PATIENT SUPPORT, all of which were filed on May 2, 2005, all of which are incorporated herein by this reference.

The present application is also related to U.S. Provisional Patent Application Ser. No. 60/636,252, entitled QUICK CONNECTOR FOR MULTIMEDIA, filed Dec. 15, 2004, which is incorporated herein by this reference.

The present application is also related to U.S. Provisional Patent Application Ser. No. 60/697,748, entitled PRESSURE CONTROL FOR A HOSPITAL BED and corresponding PCT application No. PCT/US06/26787 filed Jul. 7, 2006, and U.S. Provisional Patent Application Ser. No. 60/697,708, entitled CONTROL UNIT FOR A PATIENT SUPPORT, and corresponding PCT application No. PCT/US06/26788 filed Jul. 7, 2006, and U.S. Provisional Patent Application Ser. No. 60/697,748 entitled PATIENT SUPPORT and corresponding PCT Application No. PCT/US06/26620 filed Jul. 7, 2006 and PCT application No. PCT/US05/14897 entitled PATIENT SUPPORT filed May 2, 2005, all of which are incorporated herein by this reference.

The present application is also related to U.S. Provisional Patent Application Ser. No. 60/821,494, entitled PATIENT SUPPORT, which was filed on Aug. 4, 2006, the disclosure of which is incorporated herein by this reference.

BACKGROUND

The present disclosure relates to support surfaces, such as mattresses. More particularly, the present invention relates to support surfaces used to support a patient on a bed frame, such as in a hospital or other patient care environment. Even more particularly, the present invention relates to support surfaces for patients that require pulmonary therapy.

Known hospital beds and mattresses are disclosed, for example, in U.S. Pat. No. 4,949,413 to Goodwin, U.S. Pat. No. 5,647,079 to Hakamiun et al., U.S. Pat. No. 5,731,062 to Kim et al., U.S. Pat. No. 6,269,504 to Romano et al., U.S. Pat. No. 6,701,556 to Romano et al., U.S. Pat. No. 6,708,352 to Salvatini et al., and U.S. Pat. No. 6,820,630 to Hand et al., all of which are assigned to the assignee of the present invention and all of which are incorporated herein reference herein in their entirety.

SUMMARY OF THE INVENTION

The present invention may comprise one or more of the features recited in the appended claims and/or one or more of the following features or combinations thereof.

According to one aspect of the present invention there is provided a patient support surface including a cover defining an interior region, a layer of three dimensional material, located at the interior region, the three-dimensional material including a network of thermoplastic fibers, an air circulation device disposed adjacent the layer of three dimensional material, and at least one of a percussion and a vibration device, located at the interior region.

According to another aspect of the present invention there is provided a patient support surface including a cover defining an interior region, a layer of three dimensional material, located at the interior region, the three-dimensional material including a network of thermoplastic fibers, an air circulation device disposed adjacent the layer of three dimensional material, and a hose, located at the interior region, including at least one connector adapted to couple to an external device.

Pursuant to another aspect of the present invention there is provided a hospital bed including a frame, to support a patient, and a support surface; located on the frame. The support surface includes a cover defining an interior region and a layer of three dimensional material, located at the interior region. The three-dimensional material includes a network of thermoplastic fibers, an air circulation device disposed adjacent the layer of three dimensional material, and at least one of a percussion and a vibration device, located at the interior region.

According to still another aspect of the present invention there is provided a patient support surface having a head end and a foot end. The patient support surface includes a cover defining an interior region, a layer of three dimensional material, located at the interior region, the three-dimensional material including a network of thermoplastic fibers, an air circulation device disposed adjacent the layer of three dimensional material, and a head elevation device, located at the head end of the patient support surface, the head elevation device including a support surface to elevate the head end of the patient support surface.

Features and other aspects of the present disclosure will become apparent to those skilled in the art upon consideration of the following detailed description of illustrative embodiments, which exemplify the best mode as presently perceived.

BRIEF DESCRIPTION OF THE DRAWINGS

The detailed description particularly refers to the accompany figures in which.

DETAILED DESCRIPTION OF THE DRAWINGS

Figure 1:
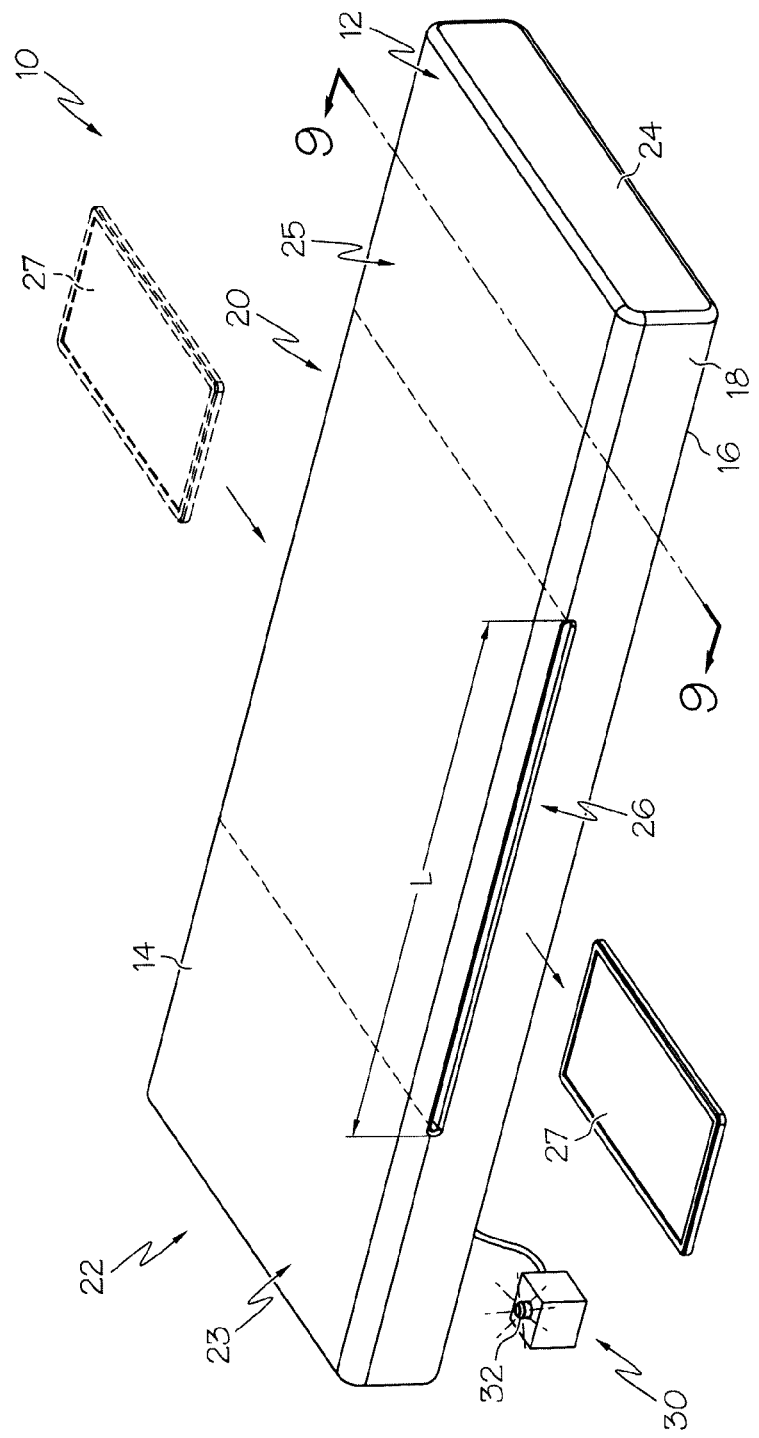
FIG. 1 illustrates a perspective view of a pressure relief support surface including a slot for an x-ray cassette.

FIG. 1 illustrates a perspective view of a pressure relief support surface 10, or mattress, including a slot 26 for inserting an x-ray cassette 27. The pressure relief support surface 10 includes a cover 12 which surrounds a plurality of components to be described later herein. The cover 12 includes a top surface 14 and a bottom surface 16, each of which is coupled together by longitudinal sides 18 and 20. A first end portion 22 located at a head end 23 of the surface 10 and a second end portion 24 located at a foot end 25 of the surface 10 complete the cover 12. Slot 26 includes an aperture located along at least one of the longitudinal sides 18, 20. Slot 26 provides for placement of an x-ray cassette 27 beneath the top surface 14 of the cover 12.

Such pressure relief support surfaces are typically used in health care facilities such as hospitals, nursing homes, and extended care facilities. The use of such surfaces is not limited to such facilities, however, and can be used where there is a need, including the home.

In the illustrated embodiment, the slot 26 extends from one side 18 of surface 10 to the other side 20. The slot 26 includes a second aperture located along the longitudinal side 20 and provides for passage of the x-ray cassette 27 from a first side 18 of the mattress 10 to a second side 20 of the mattress 10. The interior region of the slot 26, located between sides 18, 20 of the mattress 10, includes a low friction material to facilitate insertion and removal of the x-ray cassette 27 without disturbing a patient positioned on the mattress 10. The slot 26 includes a length, L, which is greater than a width, W, of the x-ray cassette 27. In addition, the longitudinal slot 26 is disposed along a central portion of the support surface 10. Accordingly, the x-ray cassette 27 can be positioned at a number of locations along the support surface and beneath a patient. While the longitudinal slot 26 is shown disposed towards a central portion of the support surface 10, the longitudinal slot can be disposed closer to the head end or the foot end portions of the support surface 10. Additional slots can be included as well. Also, the length L of the slot is not fixed but can be selected to accommodate a variety of sizes of x-ray cassettes 27 as well as to accommodate a variety of positions of the x-ray cassette 27 beneath a patient. For instance, the slot 26 as illustrated enables the caregiver to position the x-ray cassette 27 along or underneath the torso portion of a patient.

The pressure relief support surface 10 includes a head of bed indicator 30. The head of bed indicator 30 includes a light 32 or other illumination device which indicates when the head of the bed (HOB) elevation passes a certain predetermined elevation. In one instance, when the head of bed elevation passes thirty degrees, the indicator 32 will light thereby indicating that the desired elevation has been reached. Because the pressure relief support service 10 can be used on any number of bed frames, including those which are fixed in a horizontal plane and those which are continuously or partially adjustable, the head of bed indicator 30 can be either permanently or detachably coupled to the support surface 10.

Figure 2:
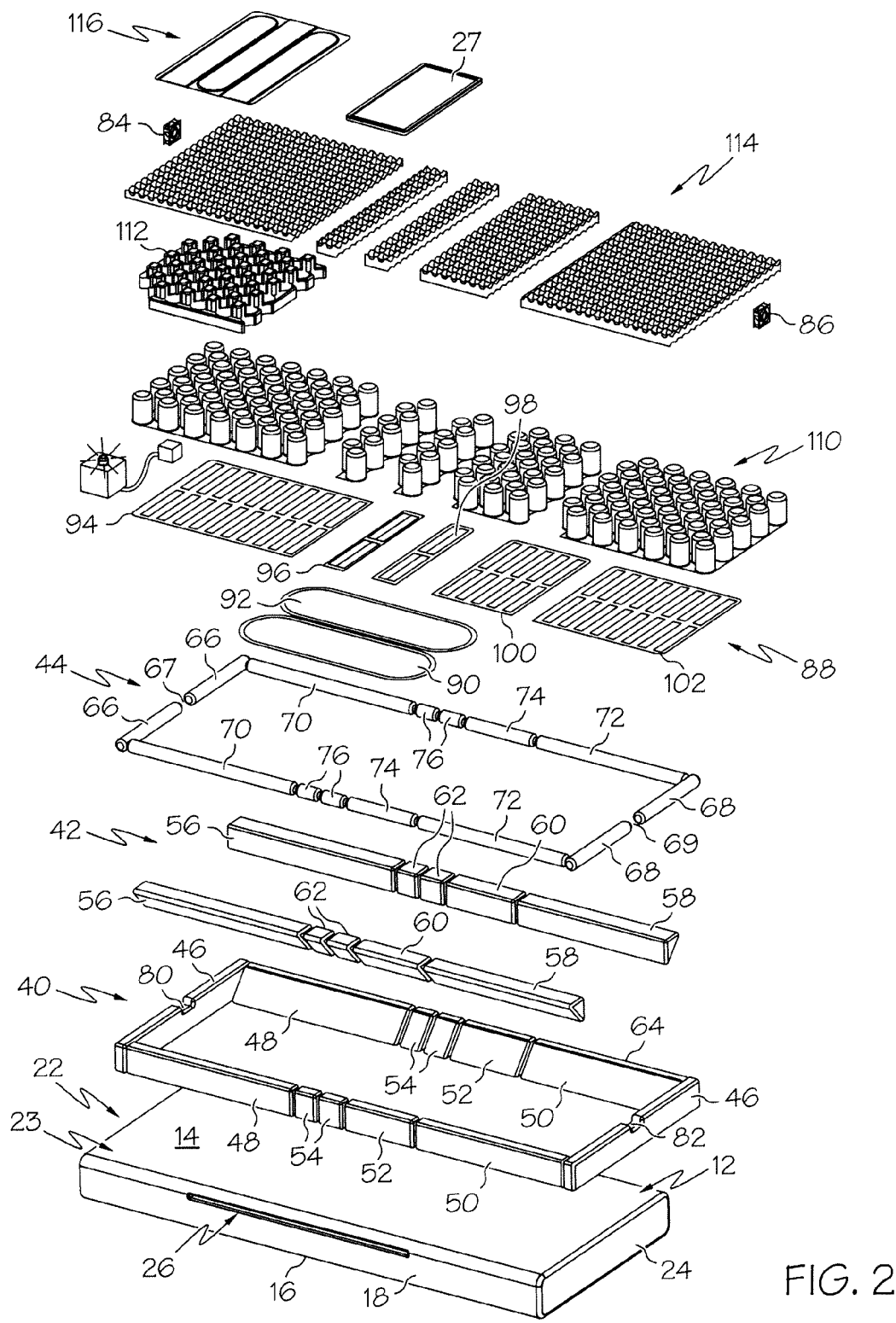
FIG. 2 illustrates an exploded perspective view of a multi-layered pressure relief support surface.

FIG. 2 illustrates an exploded perspective view of the multilayered pressure relief support surface 10. As illustrated in FIG. 2, the cover 12 including the slot 26 is shown at the bottom of the figure and is separated from the remaining layers or components of the pressure relief support surface 10. A perimeter cushion system is disposed within the cover 12 and includes a first section or portion 40, a second section or portion 42, and a third section or portion 44. The perimeter cushion system provides a side and end support of the support surface 10 such that a patient subjected to either turn assist or rotational therapy, to be described later herein, can be cradled to help maintain the patient's location within a central portion of the surface 10.

The first section 40 includes a plurality of pieces as illustrated each of which can be either completely separated from an adjacent piece or coupled thereto but still including therebetween a separation line. The use of distinct individual pieces either completely separated or coupled to adjacent pieces provides for articulation of the support surface 10 when used on an articulateable frame. As can be seen, the first section 40 includes first and second end portions 46, first and second head end portions 48, first and section foot end portions 50, first and second thigh portions 52, and first, second, third, and fourth middle portions 54. While a predetermined number of individual portions are illustrated, it is possible to incorporate more or less portions than shown depending on the application of the mattress and its use with a bed frame.

Each of the portions 48, 50, 52, and 54 include an angled side wall which creates an interfacing surface with angled side walls of the individual portions of the second section 42. The second section 42 includes first and second head end portions 56, first and second foot end portions 58, first and second thigh portions 60, and first, second, third, and fourth middle portions 62.

Each of the portions of the second section 42 include angled side walls which cooperate with and which contact the angled side walls of the portions of the first section 40 corresponding thereto. The height of the portions of the second section 42 are less than the height of the individual portions of the first section 40. When the second section 42 is placed within the first section 40, each of the portions 42 cooperate to define a substantially horizontal surface 64 upon which the third section 44 can be placed.

The third section 44 includes a plurality of perimeter bolsters including first and second head end portions 66, first and second foot end portions 68, first and second head end side portions 70, first and second foot end side portions 72, first and second thigh portions 74, and first, second, third and fourth middle portions 76. Each of the portions of the third section 44 are separable from adjacent portions or are coupled for flexibility when used with an articulated deck. In addition, the first and second parts of the portion 66 are spaced apart to define a gap 67 and a similar space or gap 69 exists between the first and second portions 68. When the first section 40, the second section 42, and the third section 44 are assembled together, the space 67 between the portions 66 and the space 69 between the portions 68 correspond to spaces, respectively 80 and 82 of the first section. The spaces 67, 69, 80 and 82 define an aperture to locate a first air circulation device or fan 84 and a second fan or circulation device 86, to be described later herein.

A plurality of pressure sensors 88 are located and disposed above turning/rotation air bladders 90 and 92. Force sensing transducers can also be used. The turning/rotation bladders 90 and 92 provide for turning a patient and/or rotating a patient under continuous lateral rotation as would be understood by one of ordinary skill in the art. The plurality of pressure sensors 88 include a first section 94, a second section 96, a third section 98, a fourth section 100, and a fifth section 102. Each of the plurality of pressure sensor sections provide a single signal which indicates a pressure amount being supported by respective sections 110 of air cushions. In particular, each section 110 can include a plurality of upstanding air cushions having a cylindrical shape. Other types of cushions or bladders are possible.

Each of the sections of upstanding cells or air cushions includes a plurality which is disposed directly upon a corresponding pressure sensor section. Consequently, when a patient lies upon the pressure relief support surface 10, patient pressures upon different portions of the surface 10 can be individually determined by the pressure or force sensor located therebelow. Consequently, pressures for head portions, upper body portions, middle portions, side portions, and leg portions, and other portions of a patient can be individualized for each patient's body.

Each of the sections 110 of cells includes upstanding cylinders or inflatable cushions which have spaces disposed therebetween. Within the spaces of the upper body section, a thermo-regulation device 112 can be disposed. The device 112 provides for thermal regulation of a patient and can cool and warm a patient. The device 112 can include any number of thermal regulation mechanisms, however, the present device 112 includes a plurality of fluid filled or water filled chambers which are disposed between the spaces of the head end section 110 for the upper body portion. As fluid or water is moved through the thermal regulation device 112, it is circulated beneath a patient to provide cooling or heating to the patient's upper body. Fluid flow or water flow can move in one direction throughout the device, as would be understood by one skilled in the art, and passes through a controlling device (not shown) which includes a pump and a mechanism for thermal regulation of the fluid.

A topper 114 is located above the sections 110. The topper includes a three dimensional material or a three dimensional fiber network made of a breathable fabric or other known three dimensional materials. One such material is known as SPACENET® material. For a further discussion of three dimensional materials, see U.S. Pat. Nos. 7,191,482; 6,701, 556; and 6,269,504; all of which are incorporated by reference herein in their entirety.

The three dimensional material 114 enables the air circulators 84 and 86 to circulate air through the topper 114. The air circulators 84 and 86 can be configured such that one of the circulators 86 is used to push air through the topper and the other air circulator is used to pull air through the topper. Consequently, air flow can be directed in a single direction.

A percussion and vibration system 116 is included and disposed at an upper body portion of the support surface 10. The percussion and vibration system provides for the percussion and vibration of a chest portion of a patient as is understood by one of ordinary skill in the art. Percussion and vibration systems are known and can include a plurality of air bladders, three of which are illustrated.

Figure 3:
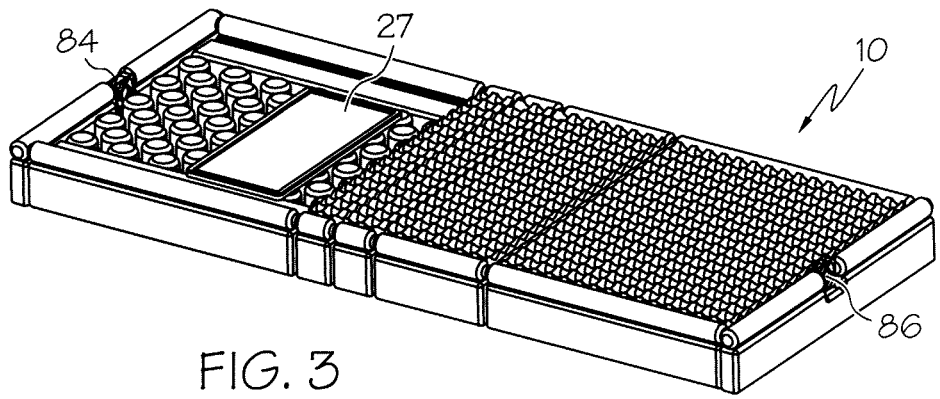
FIGS. 3, 4, and 5 illustrate a perspective view a pressure relief support surface and an x-ray cassette at is passes through a slot.
Figure 4:
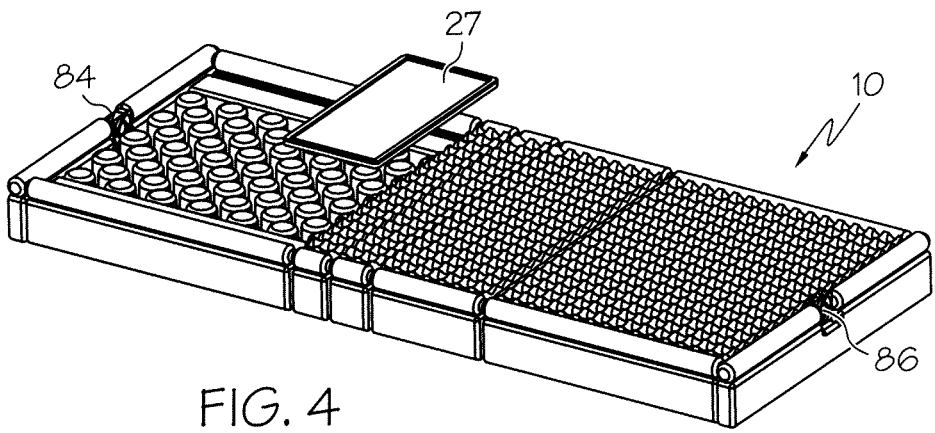
Figure 5:
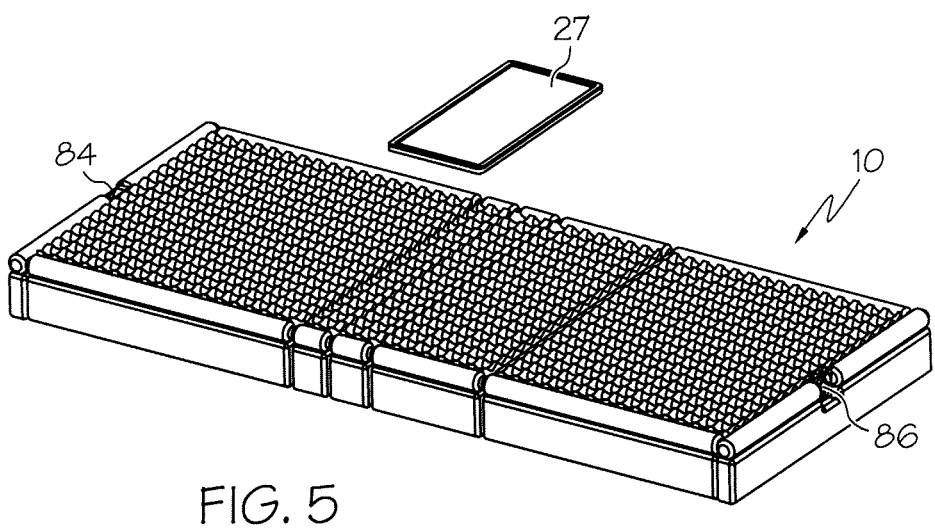

FIGS. 3, 4, and 5 illustrate a partial perspective view of the x-ray cassette 27 as it passes through the slot 26. While FIGS. 3 and 4 do not illustrate one of the portions of the topper 114, the x-ray cassette 26 when in use can be located above the upper body portion of the topper 114.

Figure 6:
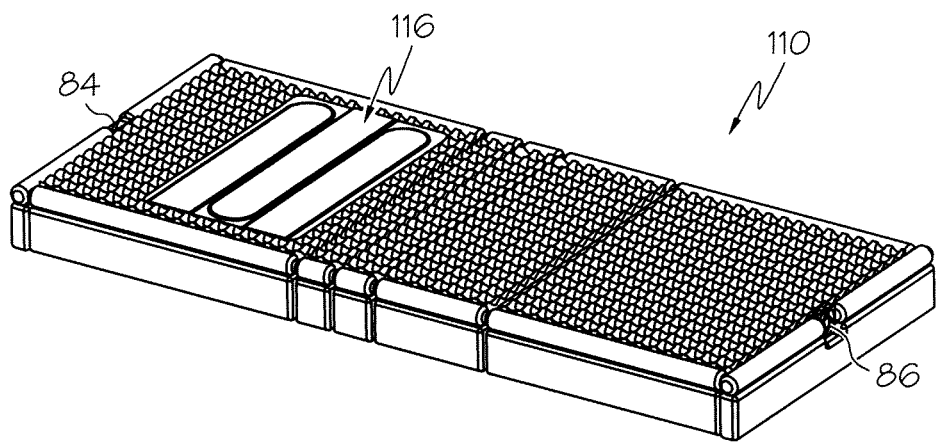
FIG. 6 illustrates a perspective view of a multi-layered pressure relief support surface including percussion and vibration bladders.

FIG. 6 illustrates a perspective view of the multi-layered pressure relief support surface 10 without the cover 12. In this illustration, the percussion and vibration bladder 116 is located in the upper body portion of the mattress 10 to provide percussion and/or vibration to the chest area of a patient.

Figure 7:
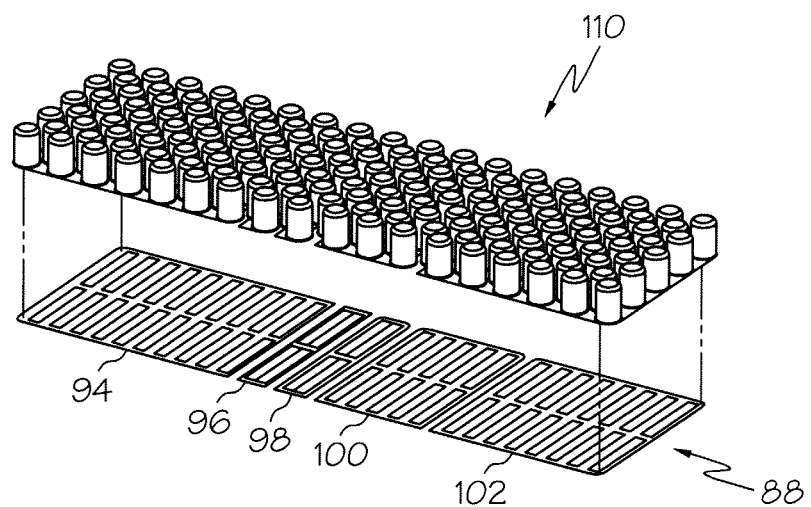
FIG. 7 illustrates an exploded perspective view of sensors with respect to cushion sections.

FIG. 7 illustrates the arrangement of the pressure sensors 88 with respect to the cushion sections 110. The individual sections 110 have been moved closer together to illustrate that the upstanding cushions when assembled provide a substantially continuous support surface without gaps between sections as is illustrated in FIG. 2. The individual sections of the pressure sensors 88 have also been moved closer together and the entire combination fits within the cavity defined by the first section 40, second section 42, and third section 44 of the perimeter cushion system of FIG. 2. In other embodiments, horizontal, laterally-oriented or log-shaped bladders may be used in place of one or more of the upstanding cushion sections.

Figure 8:
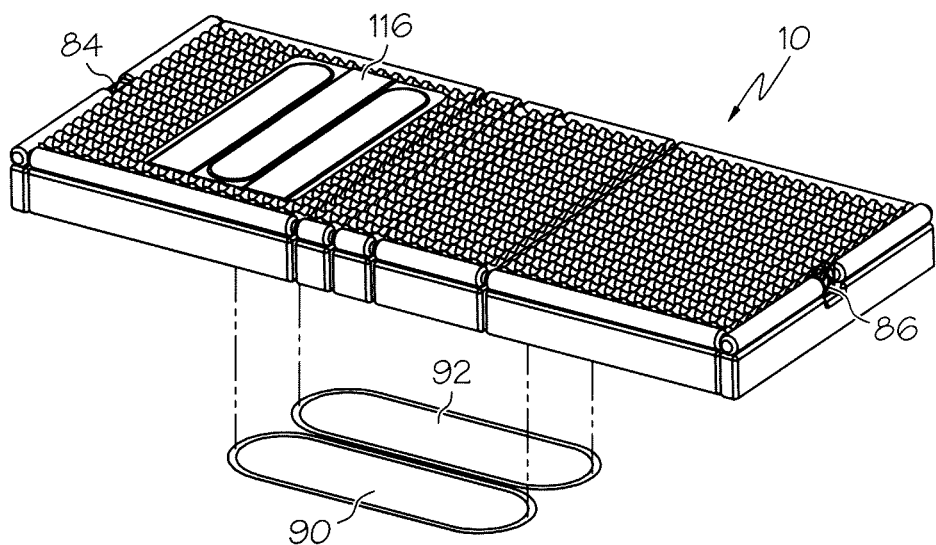
FIG. 8 illustrates a perspective view of a multi-layered pressure relief support surface with turn assist bladders.

FIG. 8 illustrates the various portions and layers of FIG. 2 excluding the cover 12 and the x-ray cassette 27. The turning/rotation bladders 90 and 92 are substantially located within a central portion of the mattress for providing turning as well as continuous lateral rotation.

Figure 9:
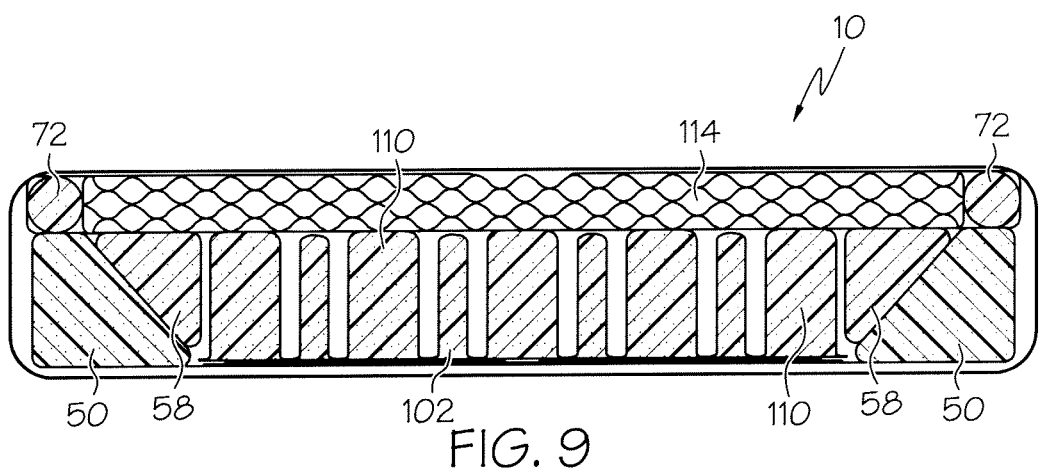
FIG. 9 illustrates a sectional view of the support surface of FIG. 1 along a line 9-9.

FIG. 9 illustrates a sectional view of the support surface 10 of FIG. 1 along a line 9-9. As previously described, and as seen here in additional detail, the portions 58 are in contact with the portions 50 of the first section 40 and define an interface therebetween along the angled side walls of each. The section 72 of the third section 44 sits upon a substantially flat and horizontally disposed top surface of the portion 50. Also, as can be seen, the upstanding cushions 110 are located above the pressure sensors 102.

Figure 11:
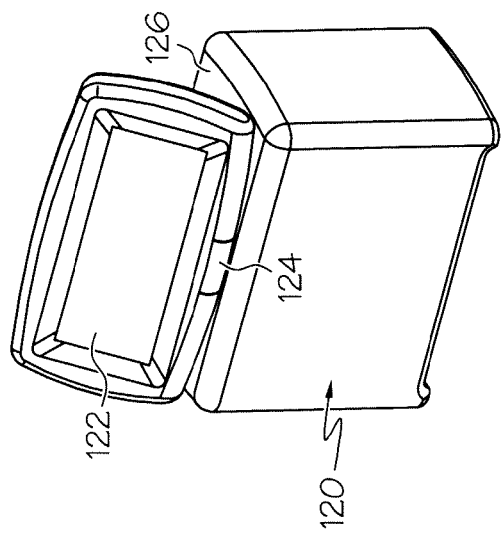
FIGS. 10-12 illustrate perspective view of a controller including user interface.
Figure 12:
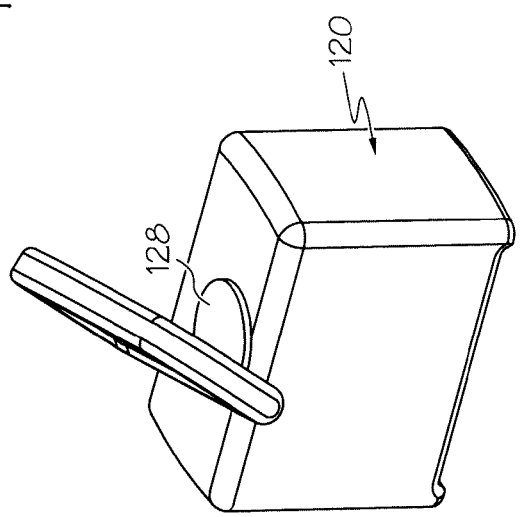
Figure 10:
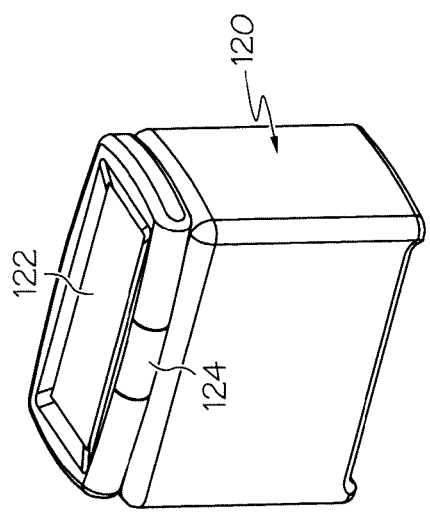

FIGS. 10-12 illustrate a controller 120 including a user interface 122. The user interface 122 is coupled to the controller 120 through a swiveling mechanism 124 which enables the 122 to lay substantially flat against a top portion 126 of the controller 120. The swiveling mechanism 124 enables the pivoting screen to move about an axis substantially parallel to the long dimension of the controller 120. The swiveling mechanism also includes a rotating portion 128 which enables the interface 122 to rotate about an axis substantially vertical with respect to the plane of the top portion 126. The swiveling mechanism 124 and rotating portion 128 in combination provide an adjustment capability which allows the pivoting interface to be moved in a variety of positions for improving access of the interface 122 to a user or caregiver. The user interface can include a variety of selectors which can include touch screen selectors, pressure sensitive buttons, and/or mechanical switches. Other later described screens can include the same selectors. The user interface can also include an electronic display, such as an liquid crystal diode (LCD) display which can display user interface screens to be described later herein.

Figure 13:
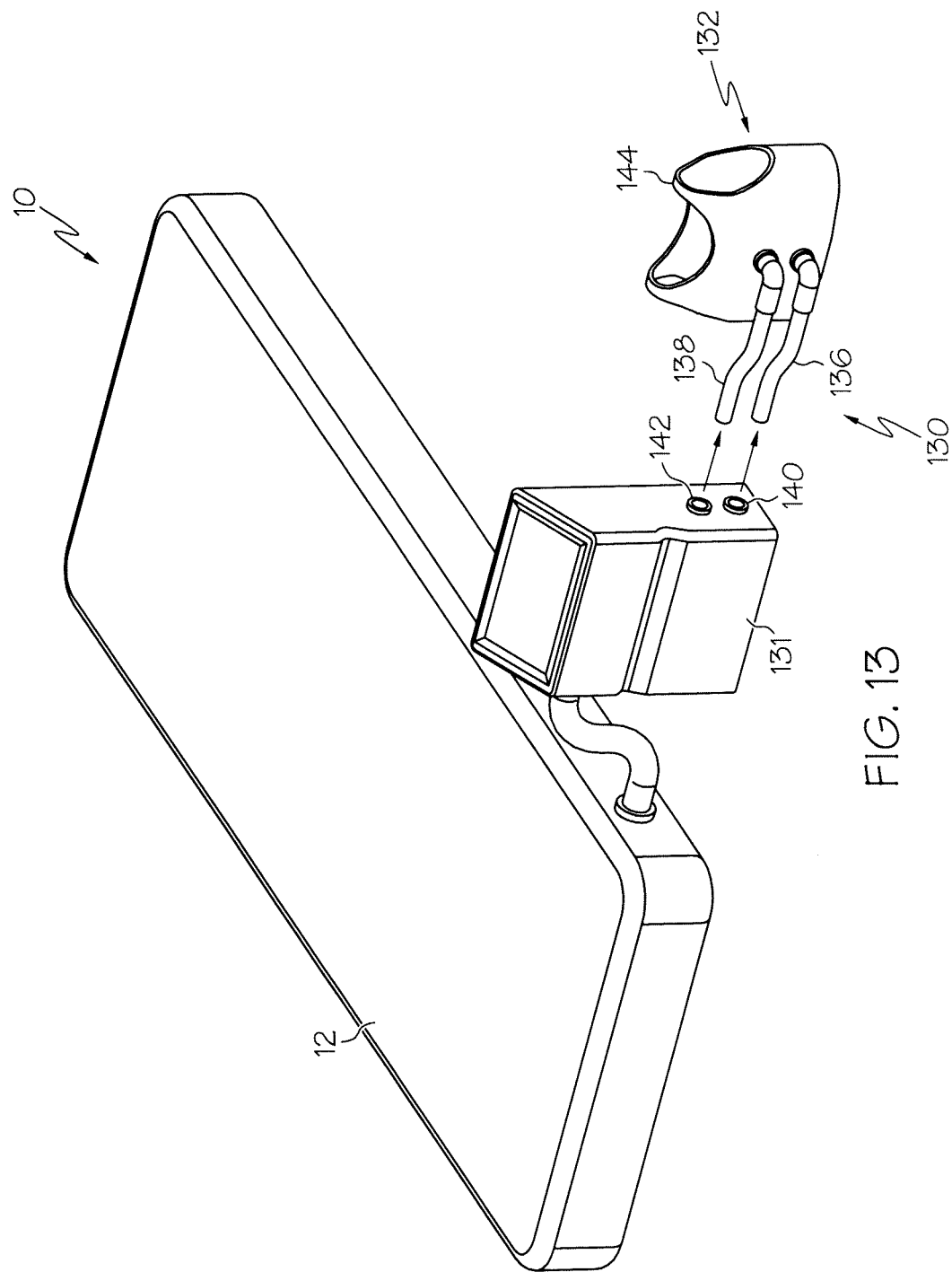
FIG. 13 illustrates a perspective view of an airway clearance system integrated with a pressure relief support surface through a control unit.

FIG. 13 illustrates a perspective view of an airway clearance system 130 integrated with a support surface through a control unit 131. The mattress or support surface 10 is illustrated with the cover 12 but not including the slot 26, which can be optional. The airway clearance system 130 includes a high frequency chest wall oscillation device 132 which is coupled to the control unit 131. One example of such a device is available from Hill-Rom, Inc. as The Vest® airway clearance system.

The control unit 131 provides for chest wall oscillation through the use of forced air which is moved through first and second tubes 136, 138 which are coupled to the controller 131 through first and second couplers 140, 142. The tubes 136 and 138 are coupled to an upper body portion 144 which surrounds the chest wall and provides high frequency chest wall oscillations for the purpose of airway lung clearance and ventilation as described in U.S. Pat. No. 6,736,785, which is incorporated in its entirety by reference herein.

Figure 14:
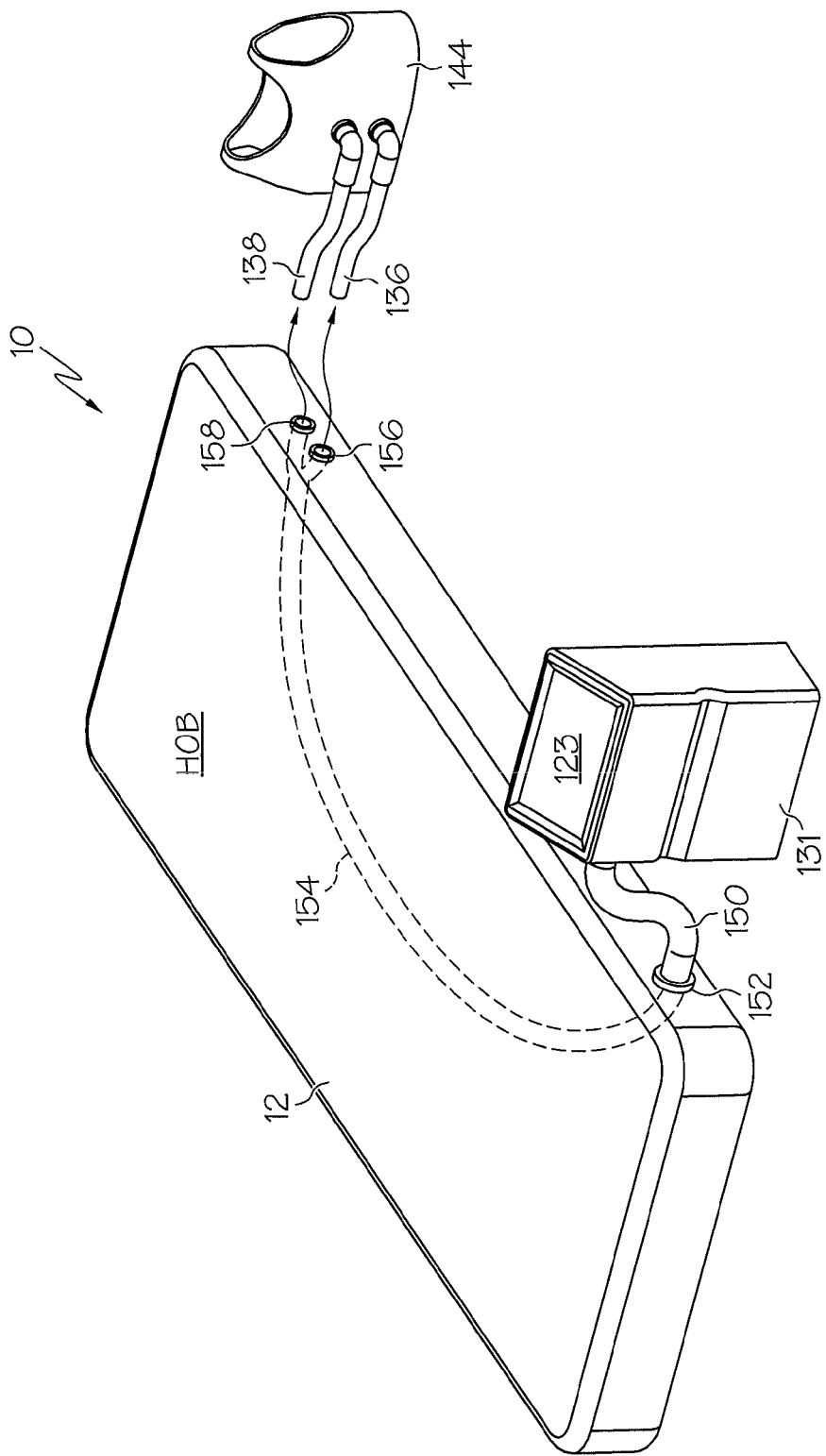
FIG. 14 illustrates a perspective view of an airway clearance system integrated directly with a pressure relief support surface.

As illustrated in FIG. 13, the controller 131 is coupled to the upper body portion 144 and enables a patient or other user who may or may not be located on the support surface 10 to use the airway clearance system 130. For instance, when a patient is sufficiently mobile to move within a facility and to sit in a chair within a hospital room, the patient can wear the upper body portion 144 when seated in a chair. As further illustrated in FIG. 14, the controller 131 can also be coupled directly to the support surface 10 through a hose 150. The hose 150 is coupled to a connector 152 which is in turn coupled to an internal hose device 154 which passes through and is incorporated in the support surface 10. A first and a second connector 156 and 158 respectively terminate the hose 150. Using this connection 156, 158 to couple to an external device, a patient lying with his or her head located at the head of the bed (HOB) can wear the upper body portion 144 when lying in bed to provide the chest wall oscillation. When controller 131 detects connection of an airway clearance system 132, controller 131 automatically disables or bypasses the mattress pulmonary therapy functions and the controller user interface 122 is automatically updated to visually indicate the status of a connection or disconnection of the airway clearance system. In this way, controller 131 can be used to control inflation and deflation of bladder portions of mattress 10 and/or to control operation of the airway clearance system 132. As such, the need to provide multiple separate control units (i.e., a mattress controller and an airway clearance system controller) may be eliminated.

Alternatively or in addition, controller 131 is sized and shaped so that a separate airway clearance system controller is stackable on top of or underneath controller 131, to thereby conserve space in the patient's healthcare environment. Controller 131 may include all or a portion of the features of control unit 120 or control unit 160.

Figure 15:
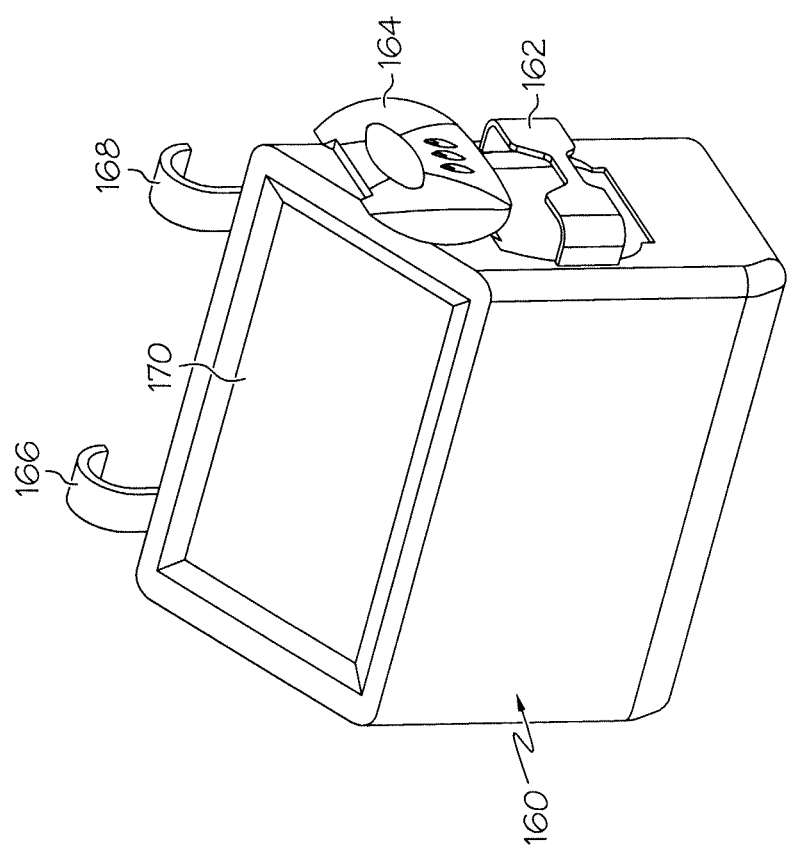
FIG. 15 illustrates a perspective view of a control unit with a holder for a deep vein thrombosis device.

FIG. 15 illustrates a perspective view of a control unit 160 having a holder 162 which can be used to support a deep vein thrombosis device (DVT) 164 by insertion into holder 162 as indicated by arrow 163. A cuff is generally provided with DVT device 164 but is not illustrated. The controller 160 includes a first attachment device 166 and second attachment device 168. Devices 166, 168 can include a first and second hook, which can be used to hang the controller 160 on a footboard, headboard, and/or side rail of a patient support frame. The controller 160 includes a user interface 170 which is fixed and coupled to the controller 160. The DVT device 164 can be used to provide pneumatic pressure to a body limb to reduce or to prevent deep vein thrombosis. For additional details, please see U.S. Pat. Nos. 6,447,467 and 6,494,852 which are incorporated herein by reference in their entirety.

Figure 16:
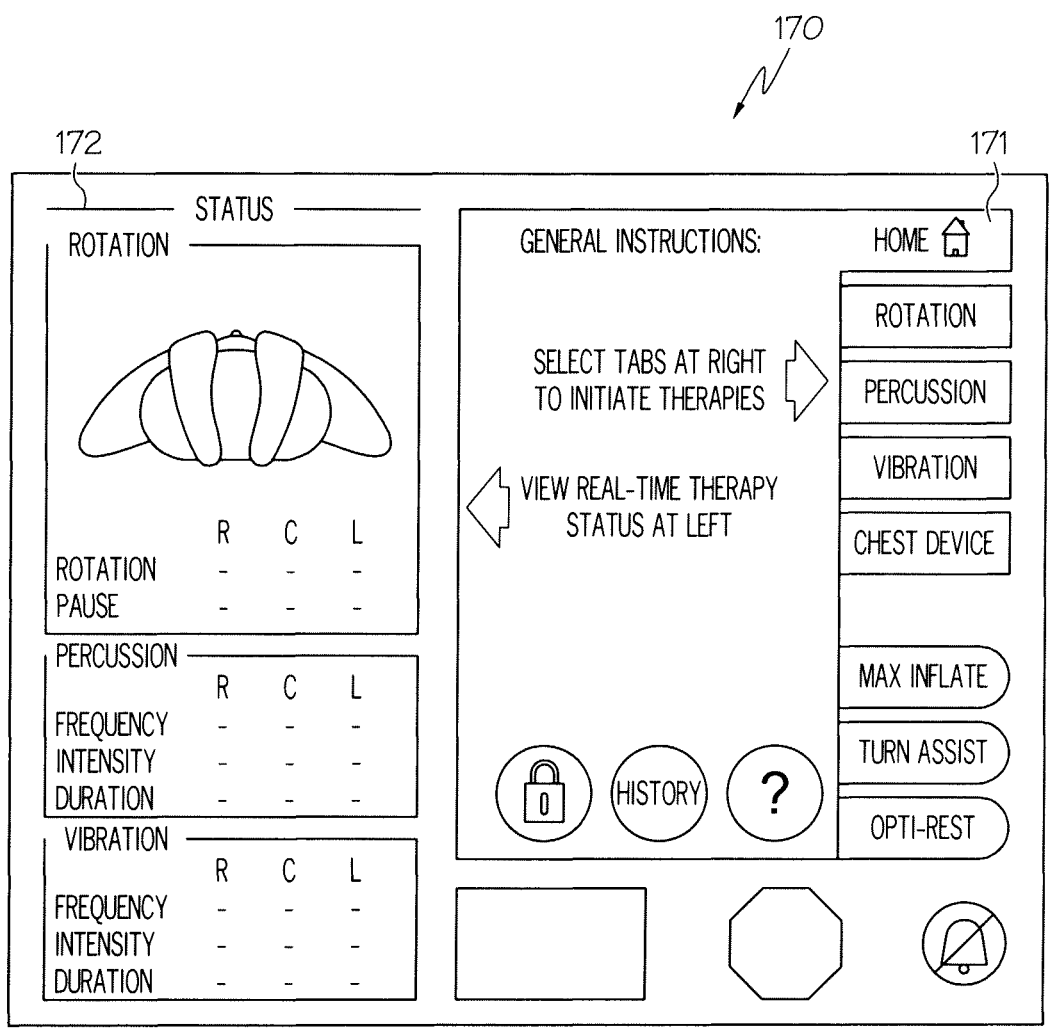
FIGS. 16-18 illustrate user interface screens of the present invention.
Figure 17:
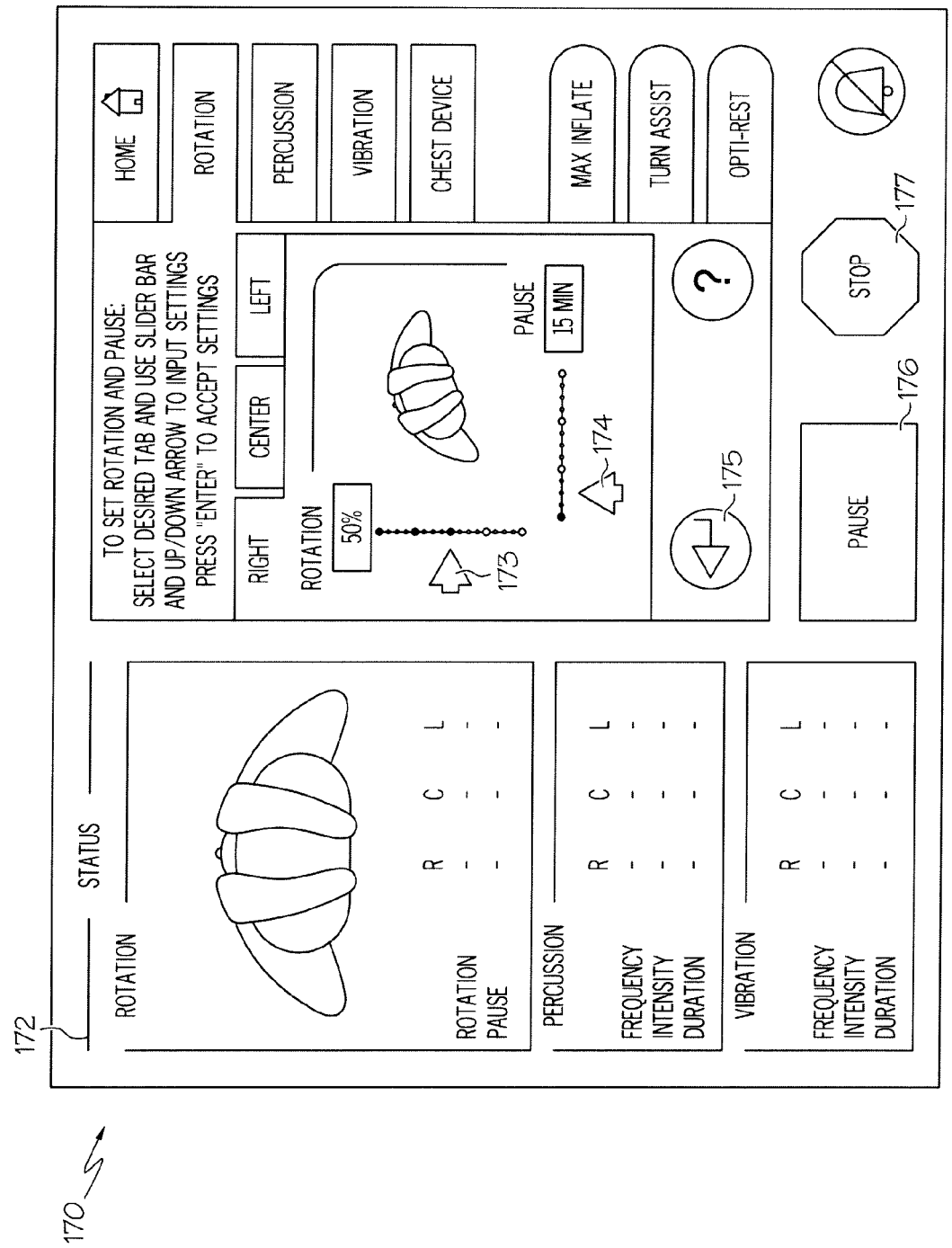
Figure 18:
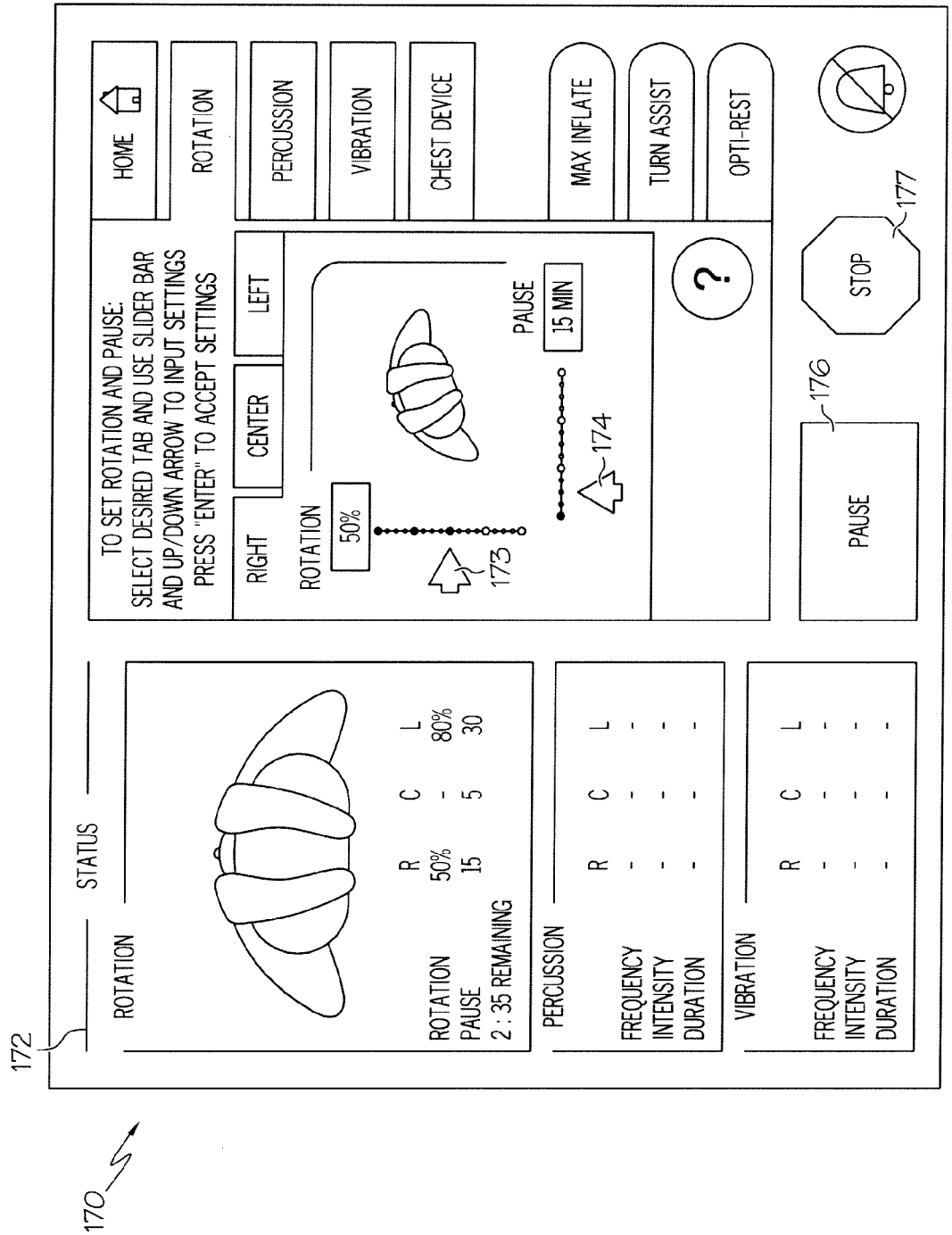

FIGS. 16-18 illustrate various user interface screens displayed on a user interface 170 such as previously described. In the illustrated embodiments, a touch screen, including a liquid crystal display (LCD) and touch sensors are used, however, it will be understood by those skilled in the art that other suitable displays and/or input-output devices may also be used. Also, in the embodiment of FIGS. 16-18, status information is generally displayed on the left-hand side of the screen while activatable buttons are generally located on the right-hand side of the screen. Each of the tabs listed down the right-hand side of the screen, i.e., "home", "rotation", "percussion", "vibration", "chest device", "max inflate", "turn assist", and "opti-rest" relates to another user interface screen comprising information and user-activatable controls relating to the identified functional capabilities. In this way, all of the available functions are displayed at all times for easy access by the user. However, in the illustrated embodiment the screen that is currently in use or active is emphasized or offset from the inactive screens by highlighting or contrasting color.

For example, as illustrated in FIG. 16, the user interface screen includes a portion 171 which is entitled "HOME". The "HOME" section enables a user to select certain tabs which initiate therapies. Those tabs can include rotation, percussion, vibration, and chest device corresponding to the chest wall oscillation device. Additional tabs are provided for adjusting mattress functions such as maximum inflate, turn assist, and Opti-rest. Opti-rest is a wave-like comfort modality with cushion pressures alternating to enhance patient comfort. A status section 172 indicates the status of rotation, percussion and/or vibration depending on which tabs have been selected on the right hand portion of the user interface 170.

As further illustrated in FIG. 17, should the rotation tab be selected, a rotation screen 170 indicates and provides the amount or percentage of rotation for a right, a center, and a left position at a status area 172. FIG. 17 illustrates an "empty" status area 172 in which no pulmonary therapy options have been initiated. FIG. 18 illustrates a status area 172 in which rotation percentages have been set and a rotation therapy is in progress. In such event, status area 172 indicates the amount of time remaining until the therapy is complete.

Slider bars, or arrows 173 and 174, can be used to select the desired settings. For instance, as illustrated in the right tab in which the right side of the body is lower than the left side, the rotation is set at 50% with the up down arrow 173. The pause time can be set to 15 minutes with the up down arrow 174. An enter button 175 is provided to finalize or to accept the settings made for pause and rotation. In addition to the right screen, a center screen and a left screen are also provided which can be selected by touching the desired center or left tab. As described with respect to the right screen, the rotation percentage and pause time can be set for both center and left. Once the right, center and left settings have been selected, the enter button 175 is selected to enter the data into the controller. The rotation screen, located below the status screen 172, indicates the values of rotation, pause, as well as time remaining. If either percussion and/or vibration is selected, the settings are made similarly as described with respect to the rotation screen and entered as necessary with the enter button. Once entered, the status screen 172 which includes a section for percussion and vibration shall illustrate the selected settings. A pause button 176 can be used to pause the selected treatments and then return to those treatments by touching the pause button a second time. Also, if it is desired to completely stop the selected treatment, the stop button 177 can be selected to stop the selected treatment as well as to clear the previously established settings.

The max inflate tab can be selected to inflate the cushions of the support system 10 to a maximum inflation, for instance, to enable a patient to enter and exit the bed more easily or to provide for cardio-pulmonary resuscitation. A turn assist tab is included and can be selected to elevate a left side or a right side of a patient to move a patient on one side or the other such that clothing and/or bed linens can be changed or removed. An Opti-Rest tab can be pressed to provide the wavelike comfort modality.

Figure 19:
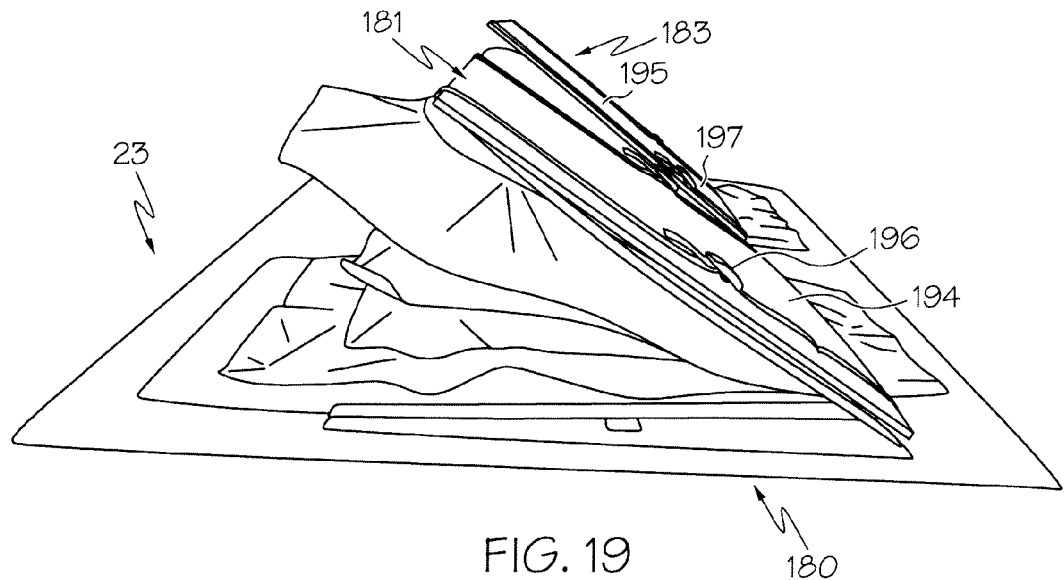
FIG. 19 illustrates an end view of one embodiment of an elevation device.
Figure 20:
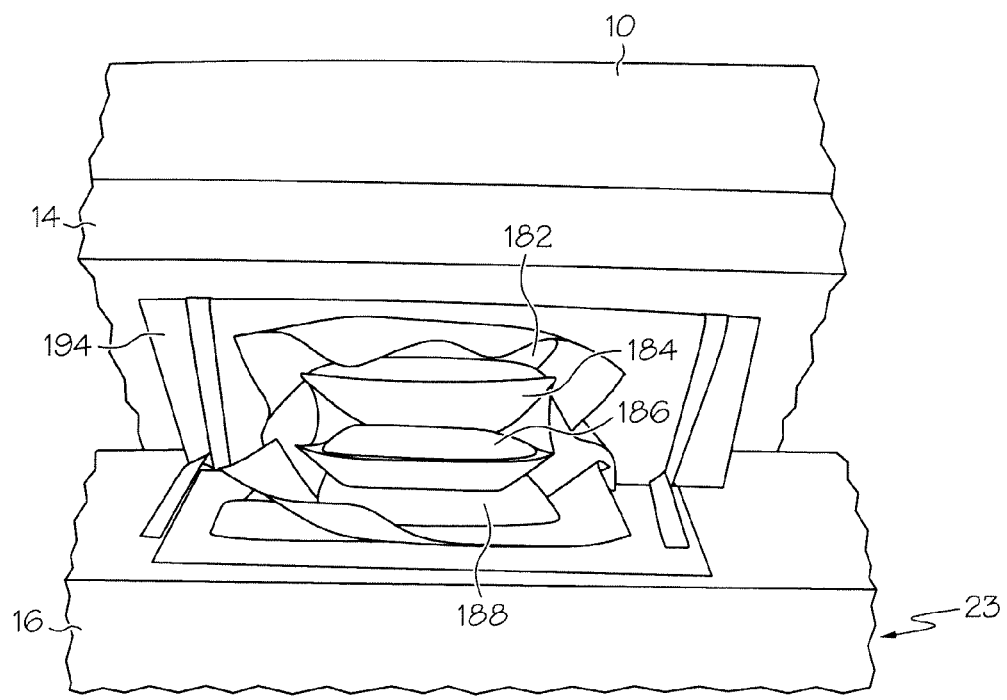
FIG. 20 illustrates a side view of one embodiment of an elevation device.
Figure 21:
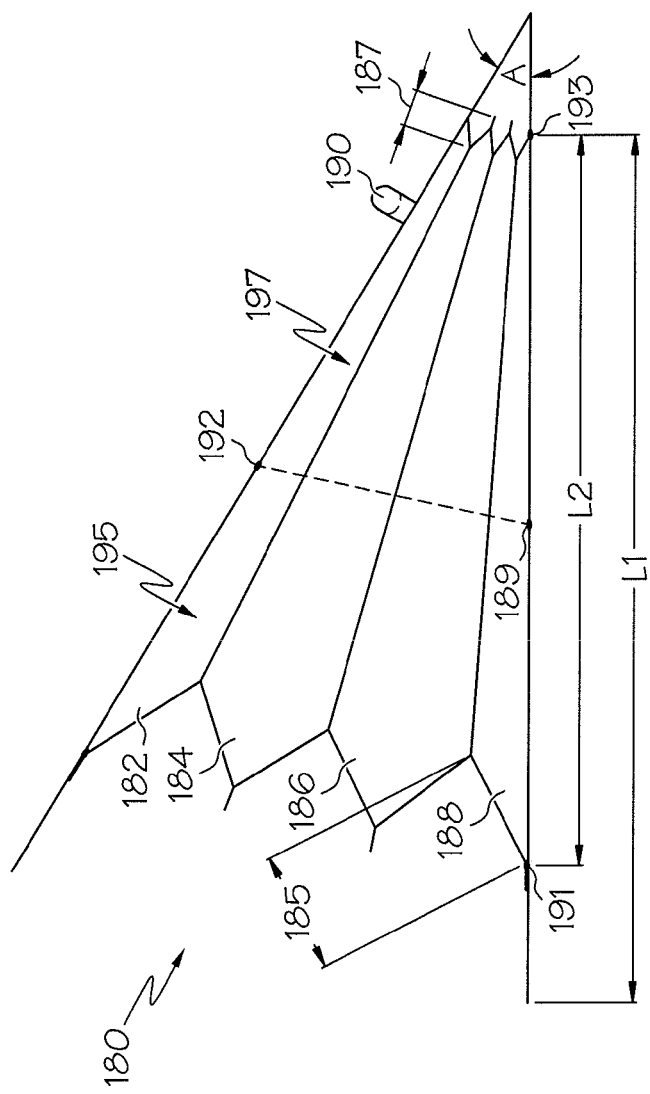
FIG. 21 illustrates a schematic illustration of FIG. 19.

FIG. 19 illustrates a head-end view of one embodiment of an elevation device 180, which may be used in place of turning/rotation bladders 90, 92. The elevation device 180 has two hinge points 191 and 193 and thereby provides a function of alternatingly elevating each lateral side of the head end of the support surface. The elevation device 180 includes a bellows type of construction as illustrated in a side view of FIG. 20 and a schematic view of FIG. 21. The elevation device 180 of FIGS. 19-21, illustrated in FIG. 19 as an end view from the head end of the mattress and in FIG. 20 as a side view from one of the sides of the mattress, includes first, second, third, and fourth compartments 182, 184, 186, and 188. Each compartment 182, 184, 186, and 188 has a first width 185, and a second width 187.

As shown in FIG. 21, an outer layer of the bellows 180 includes a first length L1 and an inner layer includes a length L2. Each compartment 182, 184, 186, and 188 has length L2. The bellows 180 includes at least one fill port 190 which is used to fill the bellows or a portion thereof with a fluid such as air. A reinforcer 192 is used around the outer compartments of the bellows 180 to help prevent distortion due to pressure variations.

In the illustrated embodiment, device 180 is configured to elevate one lateral side of mattress 10, relative to the other side, and another device 180 may be positioned laterally adjacent the first device 180 to elevate the other lateral side of the mattress 10. For instance, one instance of device 180 is positioned to provide turning assistance or rotational therapy to a patient's left side while another instance of device 180 is positioned opposite the first instance of device 180, across the width of the mattress 10, to provide turning assistance or rotational therapy to a patient's right side. In this embodiment, the first width 185 of compartments 182, 184, 186, 188 is larger than the second width 187 so that when fluid is provided through port 190 the bellows shape is created such that the height of the device 180 on the side of the compartments 182, 184, 186, 188 containing the first width 185 is higher than the height of the device on the side containing the second width 187, in order to provide the specified turning or rotation angle "A".

In one alternative embodiment, referred to herein as the "dual hinge" embodiment, reinforcer 192 also comprises an internal air flow barrier along the dashed line between points 189 and 192 of FIG. 21, which extends into the interior region of compartments 182, 184, 186, and 188 to control air flow between first and second portions 195, 197 of the compartments 182, 184, 186, and 188. As a result, air can be held in either portion 195 or portion 197 to provide turning assistance, or air can be alternatingly exchanged between portion 195 and 197 to provide rotational therapy. In the dual hinged embodiment, when portion 195 of compartments 182, 184, 186, and 188 is inflated, device 180 is hinged at point 193. When portion 197 of compartments 182, 184, 186, and 188 is inflated, device 180 is hinged at point 191. In the dual hinged embodiment, first and second widths 185, 187 are substantially the same.

As can be seen in FIGS. 19 and 20, device 180 comprises a pair of longitudinally spaced bellows 181, 183 that may be operable either in concert or independently to provide turning assistance or rotational therapy. Each device 181, 183 includes a substantially rigid support 194, 195, which rests upon the top portion of the bellows 180 and is held thereto by straps 196, 197. The substantially rigid support 194 provides for a supporting surface during elevation and rotation of the head or torso portion of the patient support 10.

The device 180 is not limited to elevation of the head or torso, but may also be used to elevate the lower extremities if placed at the foot end of the support surface. For example, either or both of sections 181, 183 of device 180 may be positioned underneath leg, calf or foot portions of a patient, and portions 195, 197 may be alternatively inflated and deflated, independently or at the same time, to exercise either or both of the knee joints of a patient positioned on mattress 10.

In one embodiment, the elevation device 180 is constructed to provide an elevation of about thirty degrees from horizontal. Other elevations are also possible, for example by inflating less than all of the compartments 182, 184, 186, and 188. To achieve a greater degree of rotation, i.e., in the range of about 45°, a portion of the surface bladders 110 may be deflated under one side 195 while the opposite bellows 197 are inflated, or vice versa. In such event, one or more perimeter bladders/supports 40, 42, 44 provide additional support to the non-elevated side of the patient. A string potentiometer, one or more ball switches, or other suitable device may be operably connected to the mattress and control unit to measure and monitor the degree of rotation provided by the portions 181, 183 of device 180.

Figure 22:
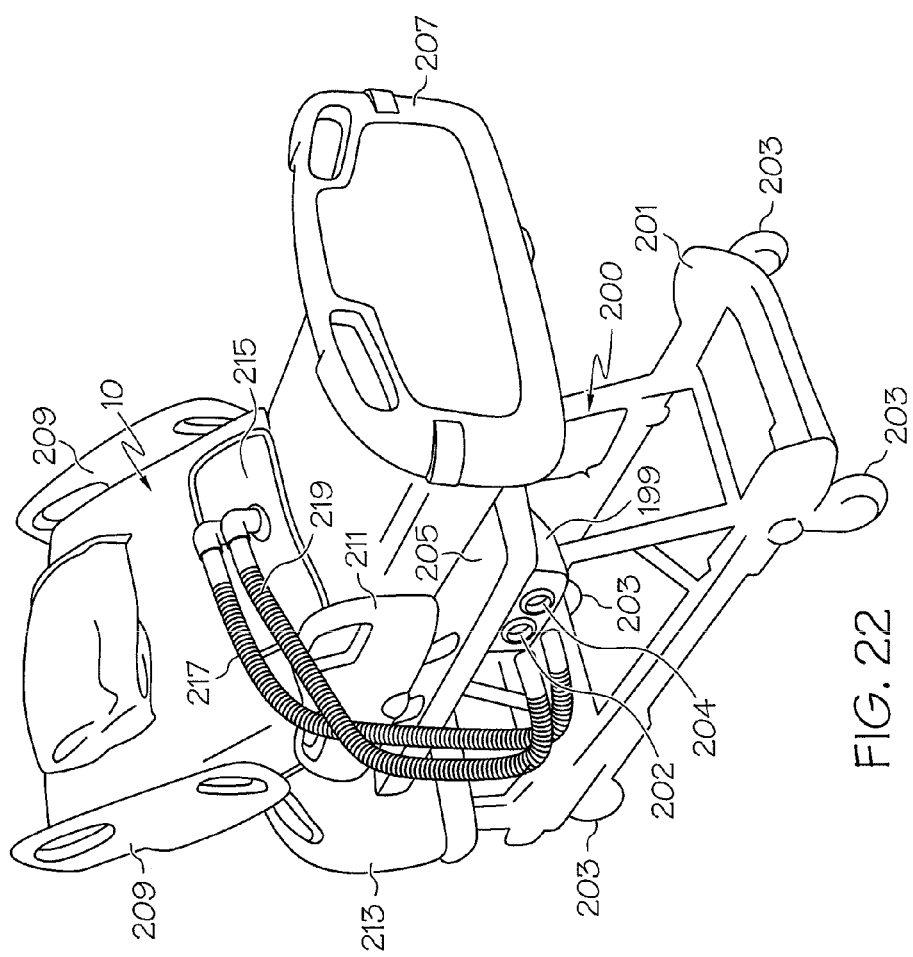
FIG. 22 illustrates a pressure relief support surface and a frame including integrated device.

FIG. 22 illustrates another embodiment of the present invention in which the support surface 10 is placed upon a frame 200 which includes and integrated device or a number of integrated components and features which interact with and provide support for the features of the support surface 10. For instance, all or a portion of the surface controls and user interfaces previously described with respect to the controllers 120, 131, 160 and also described later herein of FIGS. 16, 17, and 18 can be integrated into the one or more of the frame siderails 209, 211. In addition, the frame 200 includes an integrated control system 199 including first and second connection ports 202 and 204 into which a high frequency chest wall oscillation device 215 can be connected via hoses 217, 219. Vest device 132 may similarly be connected to ports 202, 204. In the embodiment of FIG. 22, aspects of the controller 131 of FIG. 13 are incorporated into the frame control system 199. Because the support surface 10 includes an integrated percussion and vibration, rotational therapy, and low air loss wound care/prevention surface, the surface/frame combination can provide a plurality of healthcare features in an integrated surface/frame combination.

Figure 23:
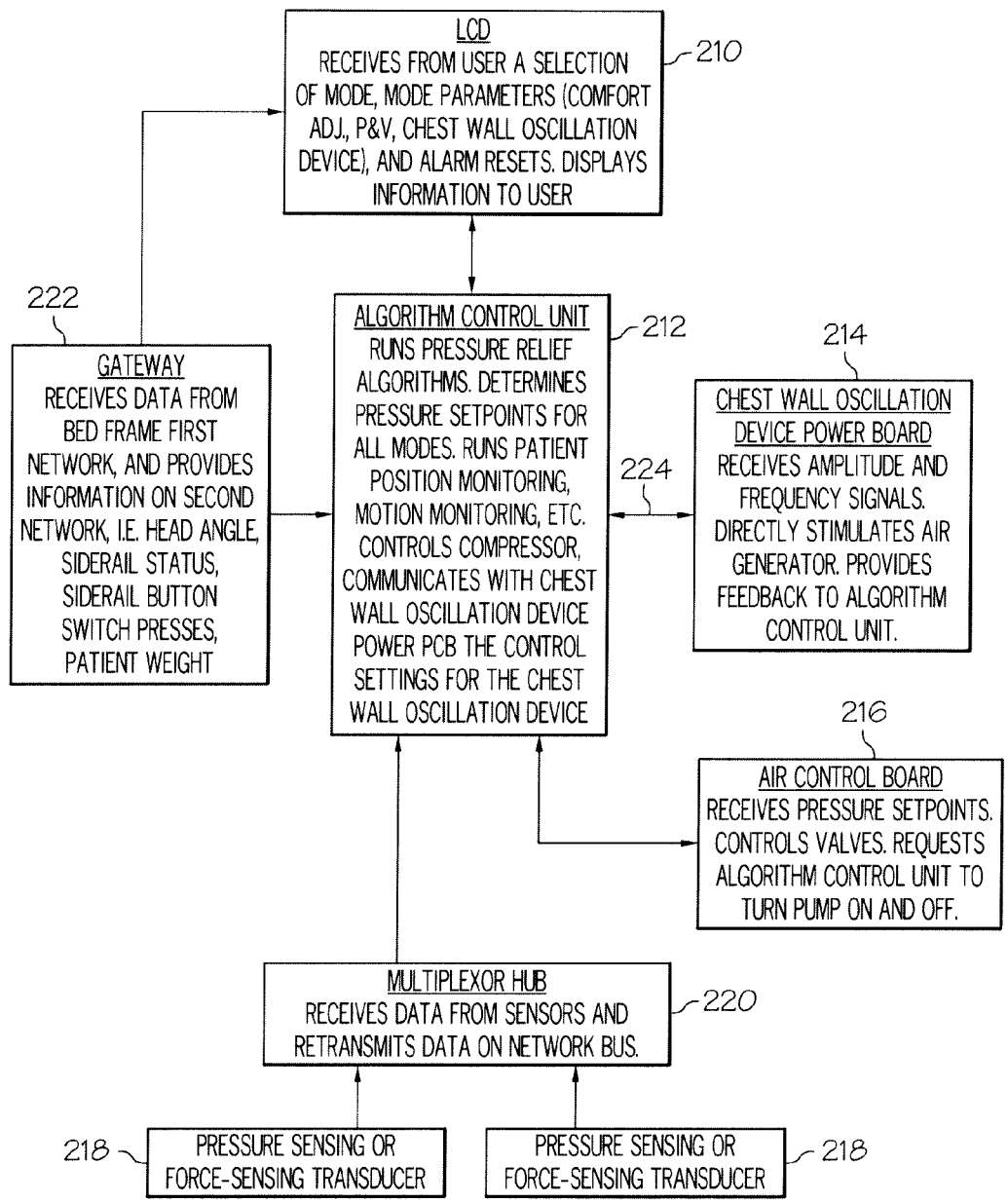
FIG. 23 illustrates a block diagram of a control and communication system.

FIG. 23 illustrates a block diagram of a bed frame or pressure relief surface control and communication system, such as controllers 120, 131, 160, 199, including controlling and communication devices to communicate with an integrated chest wall oscillation device such as device 132 or device 215. The communication system includes a liquid control display (LCD) device or other user interface device 210 which receives from a user a selection of mode, mode parameters and alarm resets. This information is displayed to the user. The parameters can include, for example, comfort adjust, percussion, vibration, and settings for the chest wall oscillation device. The user interface screen is coupled to an algorithm control unit 212 which processes pressure relief algorithms for the pressure relief surface. In addition, pressure setpoints are determined by the algorithm control unit 212 and also algorithm control unit 212 also processes patient position monitoring, motion monitoring, and controls a compressor. The unit 212 also communicates with the chest wall oscillation device, power printed circuit board (PCB) and provides the control settings for the chest wall oscillation device.

The algorithm control unit 212 communicates and is coupled to the chest wall oscillation device power board 214 by a connection 224, described further below. The power board 214 receives amplitude and frequency signals and directly stimulates the air generator for the chest wall oscillation device. The power board 214 also provides feedback to the algorithm control unit 212.

An air control board 216, which can be located within the pressure relief surface 10 or which can be located in one or more of the previously described controllers, is also coupled to the algorithm control unit 212. The air control board 216 receives pressure setpoints which have been set in the algorithm control unit 212 as well as controls the valves in response to instructions either provided by the algorithm control unit 212 or which have been set by a user at the user interface or LCD 210. The air control board 216 also generates requests to the algorithm control unit 212 to turn the pump ON and OFF which controls the pressure in the individual air cushions or bladders.

The support surface 10, as previously described, includes pressure sensing or force sensing transducers 218. These pressure sensing or force sensing transducers 218 are coupled to a multiplexor hub 220 which is, in turn, coupled to the algorithm control unit 212. The multiplexor hub 220 receives data from the transducers or sensors and retransmits the data on a bus which is located in the communication system described in FIG. 23. The bus is a network bus and the network can be of one or more types, including an ECHELON network and/or controller area network (CAN). To provide communication between the bed frame and various other described features, a gateway device 222 receives data from the bed frame first network and provides information on a second network. The second network transmits signal information such as head angle, side rail status, side rail button, switch presses, and patient weight. The first network in the described embodiment can include an ECHELON network and the second network can include a CAN.

Interfacing an airway clearance system as a component in the mattress system may reduce the number of components required to be provided in the airway clearance system controller or eliminate the need for a separate controller. For instance, a local display may not be required at the airway clearance controller since the mattress controller display can be used to show airway clearance information and controls. Also, power and motor control may be shared by the two systems. This combined architecture requires isolation and grounding issues to be addressed.

Accordingly, connection 224 may include an AC isolation transformer and be configured to use the local ground as the system reference. For example, a 5 Amp AC isolation transformer may be used to isolate the airway clearance system board 214 from the AC supply, and allow the connection of the airway clearance system board 214 to the mattress system ground. If an isolation transformer is used, and an additional power relay is used to control the power to the airway clearance system board 214, Table 1 illustrates signals that may be used to communicate from the algorithm board 212 to the airway clearance system board 214.

TABLE 1

| SIGNAL | TYPE | DESCRIPTION |
| --- | --- | --- |
| BLOWER_REQ | OUT | PWM to DC signal - control blower speed |
| BLOWER_HALL | IN | Hall sensor - blower motor speed |
| DIAPHRAGM_REQ | OUT | PWM to DC signal - control diaphragm speed |
| DIAPHRAGM_HALL | IN | Hall sensor - diaphragm motor speed |
| POWER_RELAY | OUT | Relay control for VEST power relay |
| VEST_PRESENT | IN | VEST system is present/powered signal |
| GND | GROUND | Signal ground - mattress side |

The POWER_RELAY signal may be used to power the airway clearance system, when requested, and the VEST_PRESENT may be used to verify that the airway clearance system is present and powered. The BLOWER_REQ signals control the blower motor voltage, and the BLOWER_HALL returns the motor speed. The DIAPHRAGM_REQ signals control the blower motor voltage, and the DIAPHRAGM_HALL returns the motor speed. Software algorithms correlate the speed and pressure.

An additional input to the algorithm processor 212 may also be needed, to detect when the airway clearance system air supply is connected to the mattress air system, rather than the actual airway clearance.

Connection 224 may alternatively include opto isolators and mechanical isolation. Optically isolated signals may be used to provide the needed airway clearance system isolation from the AC system. This configuration allows the airway clearance system board 214 to remain directly connected to the AC supply, and provides an interface with opto isolators in each direction to provide an isolated communication path between the algorithm board 212 and the airway clearance system board 214. This approach may require a level of mechanical isolation to ensure isolation. A relay controlled by the algorithm board 212 may be provided between the AC source and the airway clearance system board 214, for additional safety and to remove power to the airway clearance system when not in use. A signal indicates the connection and/or powering of the airway clearance system board 214.

If the opto isolator approach is used, and an additional power relay is used to control the power to the airway clearance system board, Table 2 illustrates signals that may be used to communicate from the algorithm board 212 to the airway clearance system 214.

TABLE 2

| SIGNAL | TYPE | DESCRIPTION |
| --- | --- | --- |
| +5 V | POWER | Interface power - mattress side |
| BLOWER_REQ | OUT | PWM to DC signal - control blower speed |
| BLOWER_HALL | IN | Hall sensor - blower motor speed |
| DIAPHRAGM_REG | OUT | PWM to DC signal - control diaphragm speed |
| DIAPHRAGM_HALL | IN | Hall sensor - diaphragm motor speed |
| POWER_RELAY | OUT | Relay control for VEST power relay |
| VEST_PRESENT | IN | VEST system is present/powered signal |
| GND | GROUND | Signal ground - mattress side |

The POWER_RELAY signal is used to power the airway clearance system, when requested, and the VEST_PRESENT is used to verify that the airway clearance system is present and powered. The BLOWER_REQ signals controls the blower motor voltage, and the BLOWER_HALL returns the motor speed. The DIAPHRAGM_REQ signals controls the blower motor voltage, and the DIAPHRAGM_HALL returns the motor speed. Software algorithms correlate the speed and pressure. Each side of the interface provides local +5V power and ground.

As additional input to the algorithm processor 212 may also be needed, to detect when the airway clearance air supply is connected to the mattress air system, rather than the actual airway clearance unit.

The opto isolators and relay may be located on the same circuit board, and may be associated with the airway clearance board 214 to minimize the exposure of the circuitry at a high voltage.

Two possible configurations for the mattress—airway clearance system interface are described above. Each approach has associated pro and cons. The opto isolated approach may have a lower electrical cost, but may have an increased mechanical cost to ensure sufficient airway clearance system isolation. The isolation transformer approach may provide a simpler mechanical design and better isolation, but may have an additional cost associated with the isolation transformer. The cost and risk associated with each approach will need to be evaluated to determine the best system approach for a particular implementation of the present invention.

The airway clearance system board interface is designed to communicate with the user interface board 210 in close proximity. If the cable distance between the algorithm board 212 and the airway clearance system board 214 is a significant distance, signal conditioning may be required, using digital signals, and an interface board may need to be located physically closer to the airway clearance system board 214. Low voltage drivers, or RS232 drivers may be used to boost the signal level. The PWM to DC filtering should be done close to the airway clearance system board 214 to minimize noise on this signal. If the opto isolated approach is used, then the signals between the daughter board and airway clearance system board may need additional optical elements.

Figure 24:
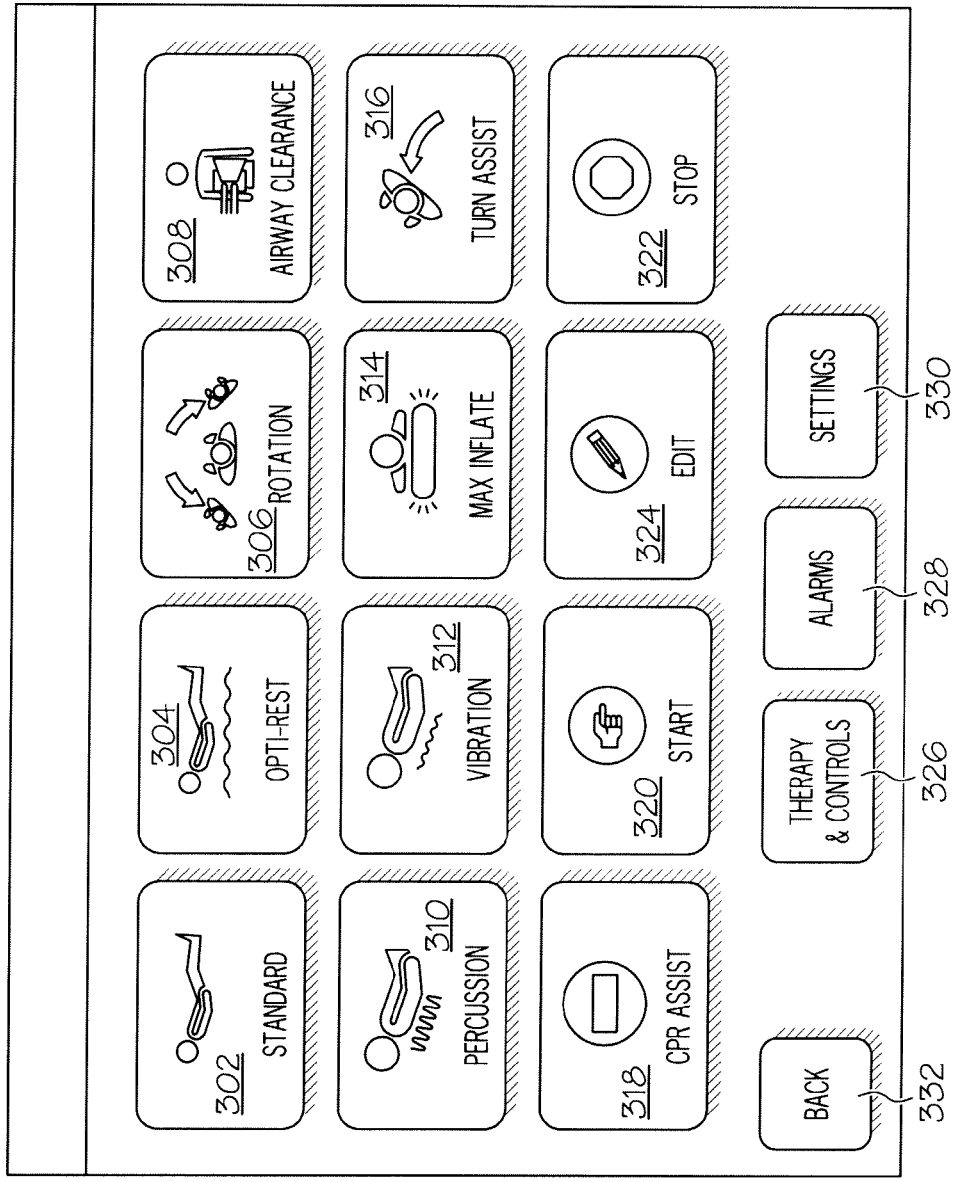
FIGS. 24-30 illustrate additional user interface screens of the present invention.

FIG. 24 illustrates one embodiment of a user interface screen which can be used on any of the previously described controllers and interfaces as well as with the bed frame described herein with reference to FIG. 22, where the interface can be embodied or incorporated into a siderail, head board, and/or footboard. As illustrated in FIG. 24, the user interface screen 300 can include a variety of selectors which can be touch screen selectors, pressure sensitive buttons, and/or mechanical switches. The features which can be accessed from the user interface screen of FIG. 24 via selectors include a standard operating mode 302, an Opti-Rest mode 304, a rotation mode 306, an airway clearance system mode 308, a percussion mode 310, a vibration mode 312, a maximum inflate mode 314, a turn assist mode 316, and a cardio pulmonary resuscitation (CRR) assist mode 318. In addition, start and stop buttons 320, 322 as well as back 332 and edit buttons 324 are available. Likewise, the user interface screen can be used to access other therapy and controls 326, setting alarms 328, and settings for a variety of features including pressure settings 330.

Figure 25:
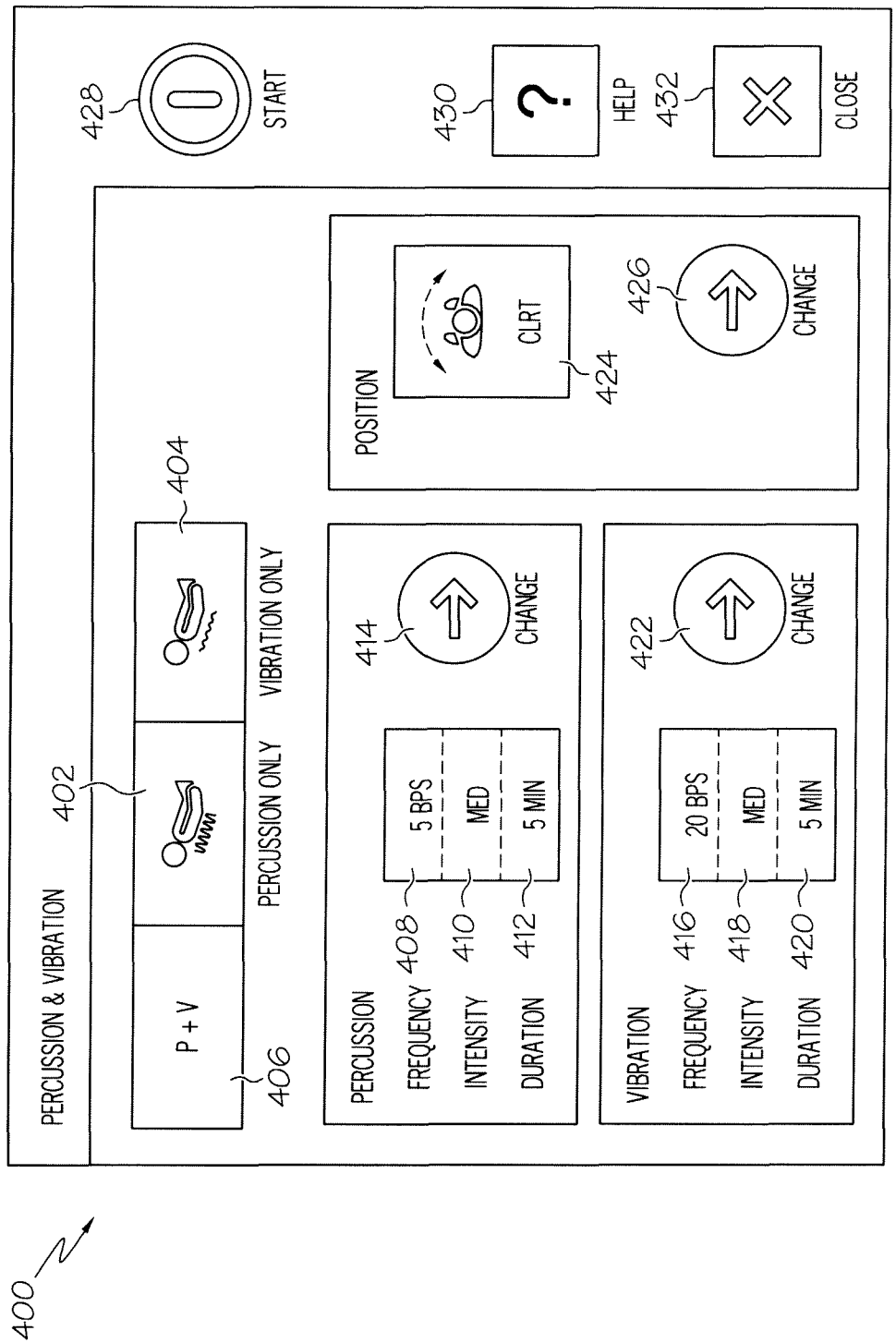

FIG. 25 illustrates one example of a user interface screen 400 where percussion and vibration parameters can be set for the mattress support 10. While FIG. 24 illustrates a single selector 310 for percussion and a single selector 312 for vibration, the user interface screen of FIG. 24 may alternatively or in addition include a single button for both percussion and vibration (P&V), which upon selection accesses the user interface screen of FIG. 25.

The user interface screen 400 of FIG. 25 enables an individual to select percussion therapy only 402, vibration therapy only 404, or both percussion and vibration therapy 406 with a P & V selector. In addition, the frequency 408, 416 intensity 410, 418 and duration 412, 420 can be set for percussion and/or vibration by selecting or activating a change selector 414, 422, respectively. The change selectors 414, 422 access a second user interface screen (not shown) where frequency, intensity, and duration can be selected or changed for the percussion and/or vibration therapy. Once the settings for frequency and/or vibration have been changed, the selected values are displayed on the user interface screen of FIG. 25. For instance, in the illustrated embodiment, percussion frequency 408 and vibration frequency 416 are selected as a function of beats per second (bps), percussion intensity 410 and vibration intensity 418 are selected as being a low, medium, or high intensity, and percussion duration 412 and vibration duration 420 are selected as a value based on the number of minutes desired for the duration to occur. The percussion and vibration screen 400 of FIG. 25 also enables the user to select and to change the values for continuous lateral rotation therapy (CLRT) via button 424. Once button 424 is selected, the preselected values for percussion, vibration and continuous lateral rotation therapy can be started by pressing the start selector 428. A help button 430 can be activated to provide user information for additional details and a close button 432 can be activated to close the displayed screen 400 and return to the screen 300 of FIG. 24.

Figure 26:
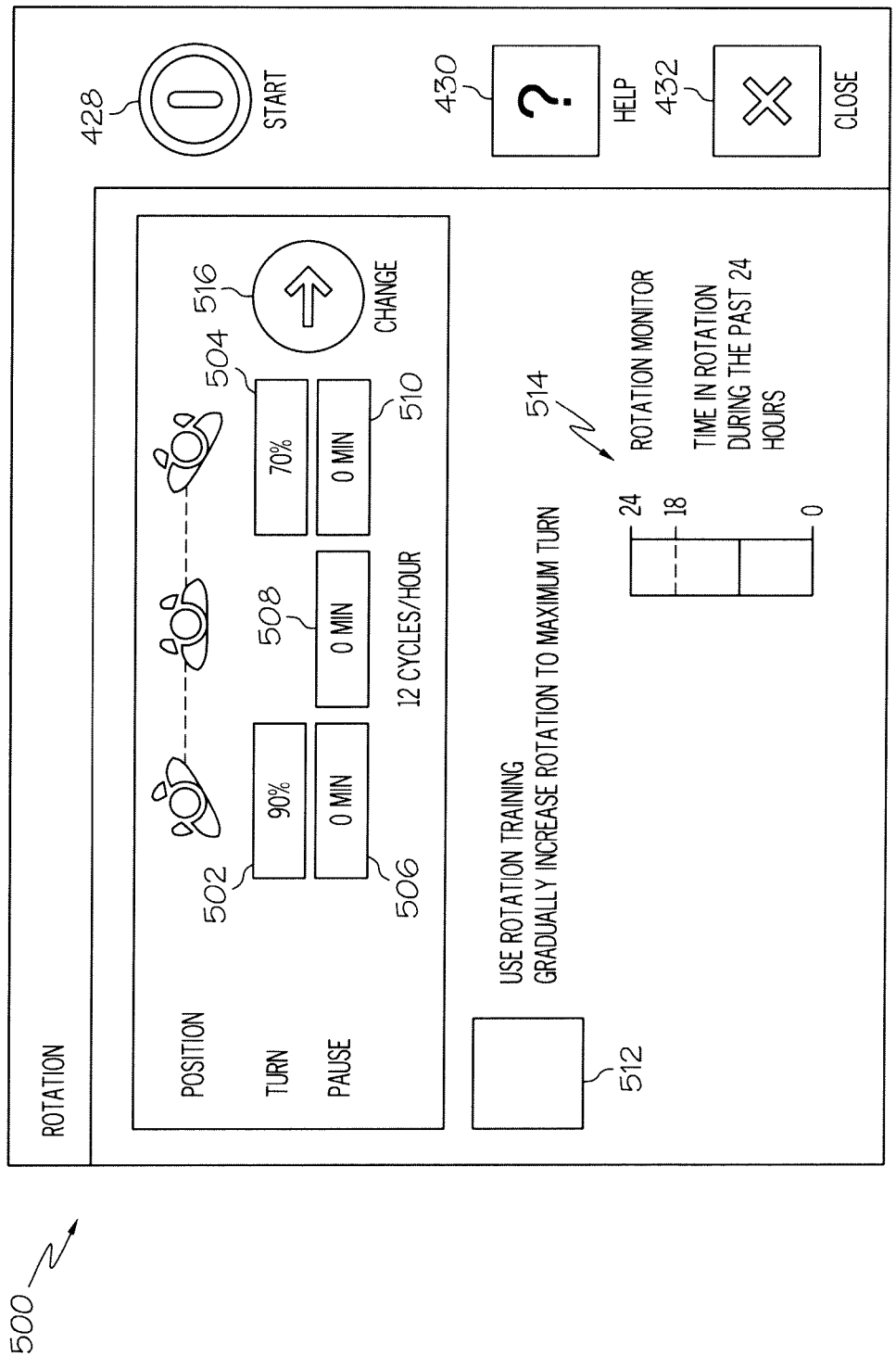

FIG. 26 illustrates one example of a rotation user interface screen 500 which has been accessed through the selection of the CLRT selector 424 of FIG. 25. The turn (rotation) percentages 502, 504 can be selected for a patient at a left turn and a right turn and the pause 506, 508, 510 in minutes can be selected to place the patient at a particular position for the selected period of time. Additionally, a use rotation training button 512 can be used to acclimate the patient to continuous lateral rotation therapy. By selection of this particular selector 512, the angle of rotation therapy is gradually increased to the maximum turn which has been selected. A rotation monitor 514 is also included and indicates the amount of time the patient has been under the rotation therapy in the most previous 24 hours.

Figure 27:
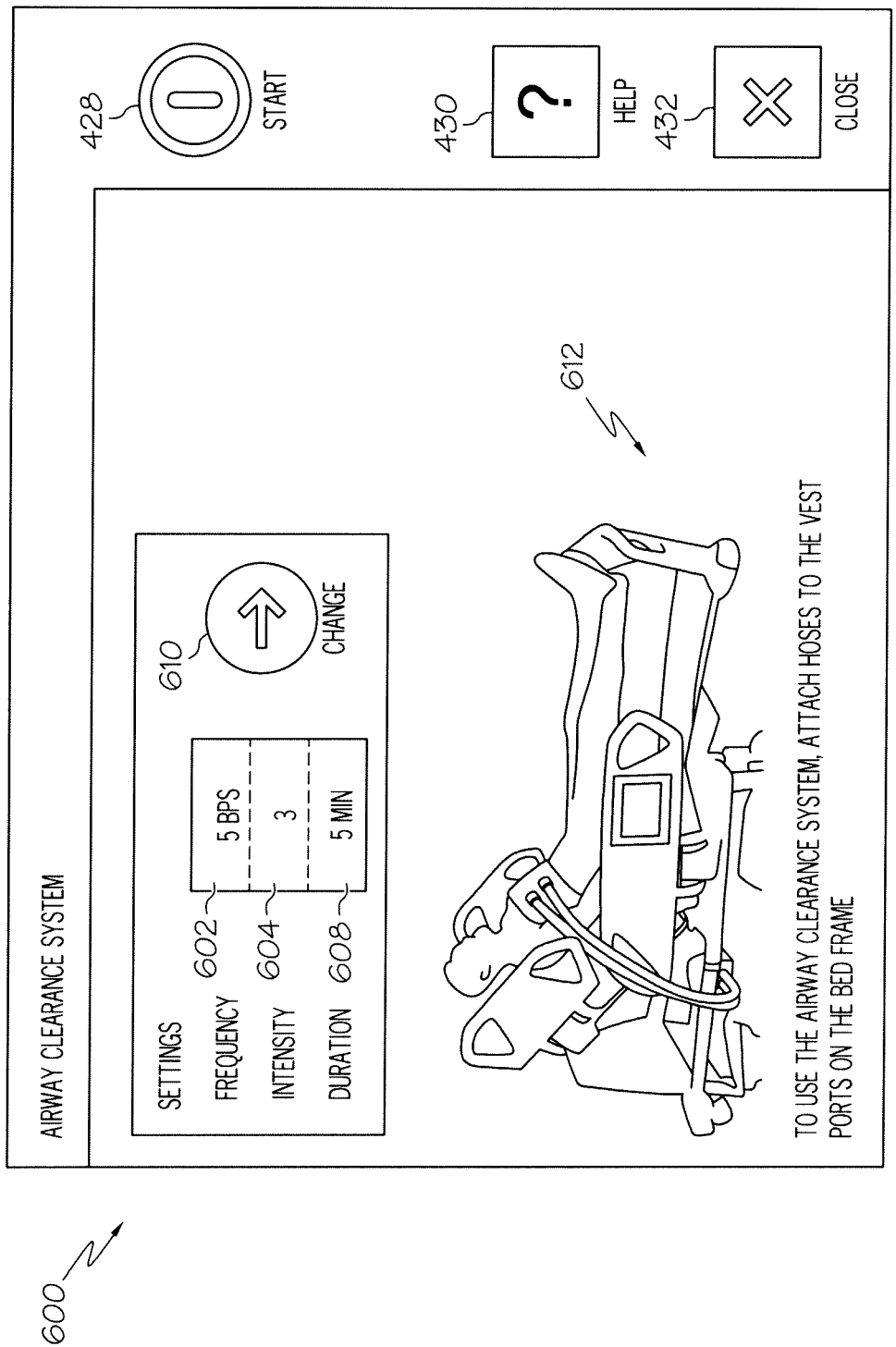

If the airway clearance selector 308 of FIG. 24 is selected, the user interface screen 600 of FIG. 27 is displayed. At this screen, a user can select the pulse frequency 602 in beats per second, the intensity 604 of pressure applied by the airway clearance system to the chest of a patient, and time duration 608 of the airway clearance therapy in minutes. Screen 600 also includes a help/training graphic and/or visual feature 612 to aid the caregiver in administering the airway clearance therapy.

Figure 28:
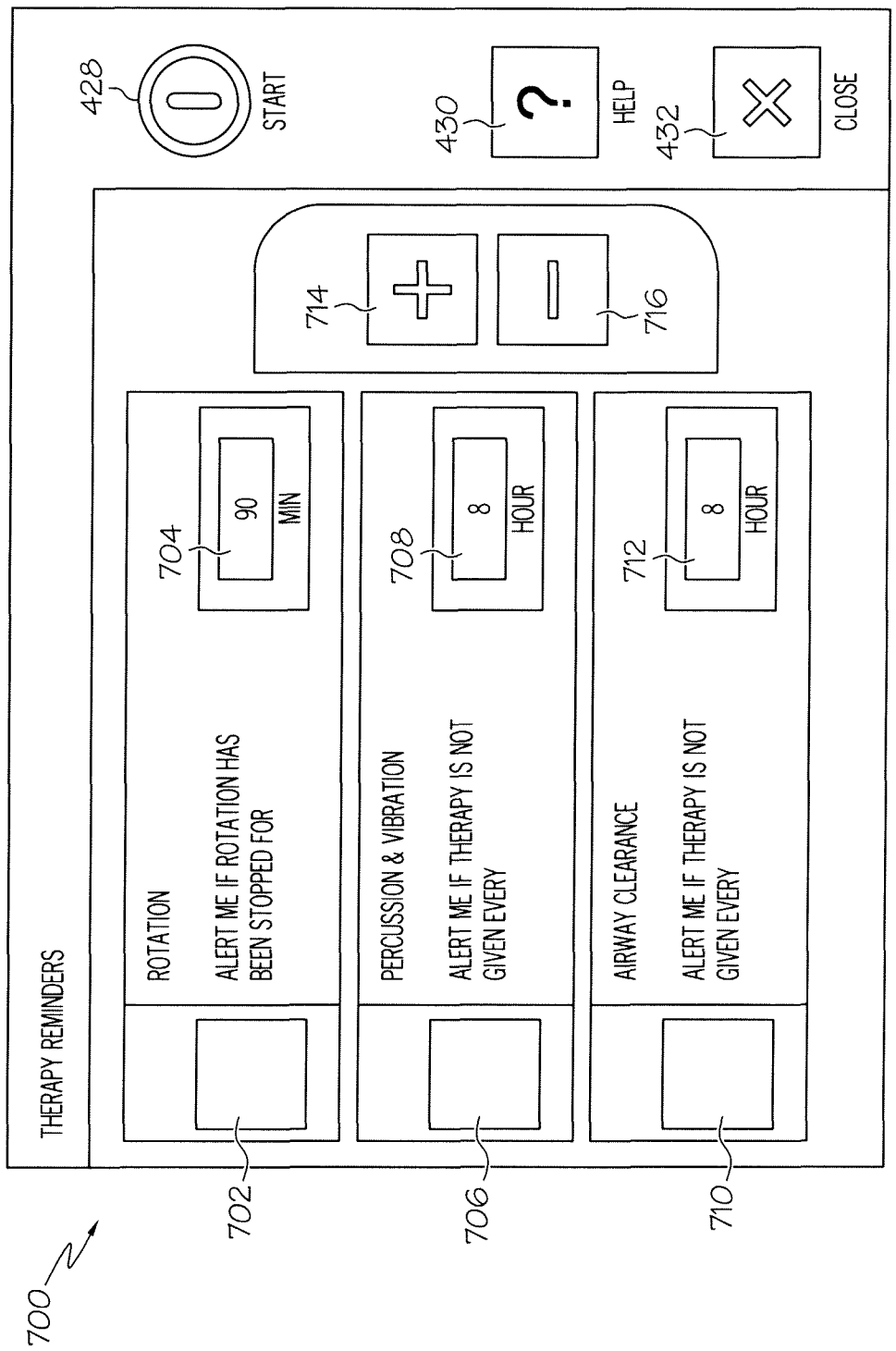

FIG. 28 illustrates a therapy reminder user interface screen 700 in accordance with the present invention. By selecting the therapy and controls selector 326 of FIG. 24, the therapy reminder screen 700 of FIG. 28 is displayed. At this screen, a user can select reminders 702, 706, 710 for the therapies of rotation, percussion and vibration, and airway clearance. The length of time between the last therapy session and the reminders is specified at areas 704, 708, 710 for each of the rotation, percussion and vibration, and airway clearance therapies, respectively. This length of time is adjusted using button 714 to increase the delay and by using button 716 to decrease the delay. Other reminders are also possible. For instance, it is possible to provide an alert if rotation has been stopped for a selected period of time, which in this case is shown to be 90 minutes. Likewise, percussion and vibration as well as airway clearance reminders can be selected for every eight hours, for instance. Once the selected time period has elapsed, an alarm, such as a visual or aural alert is made to indicate that it is time to provide the therapy. While the figures show reminders and other parameters configured for each of the available therapies, it will be understood by those skilled in the art that any combination of the available therapies may be activated or deactivated at a given time.

Figure 29:
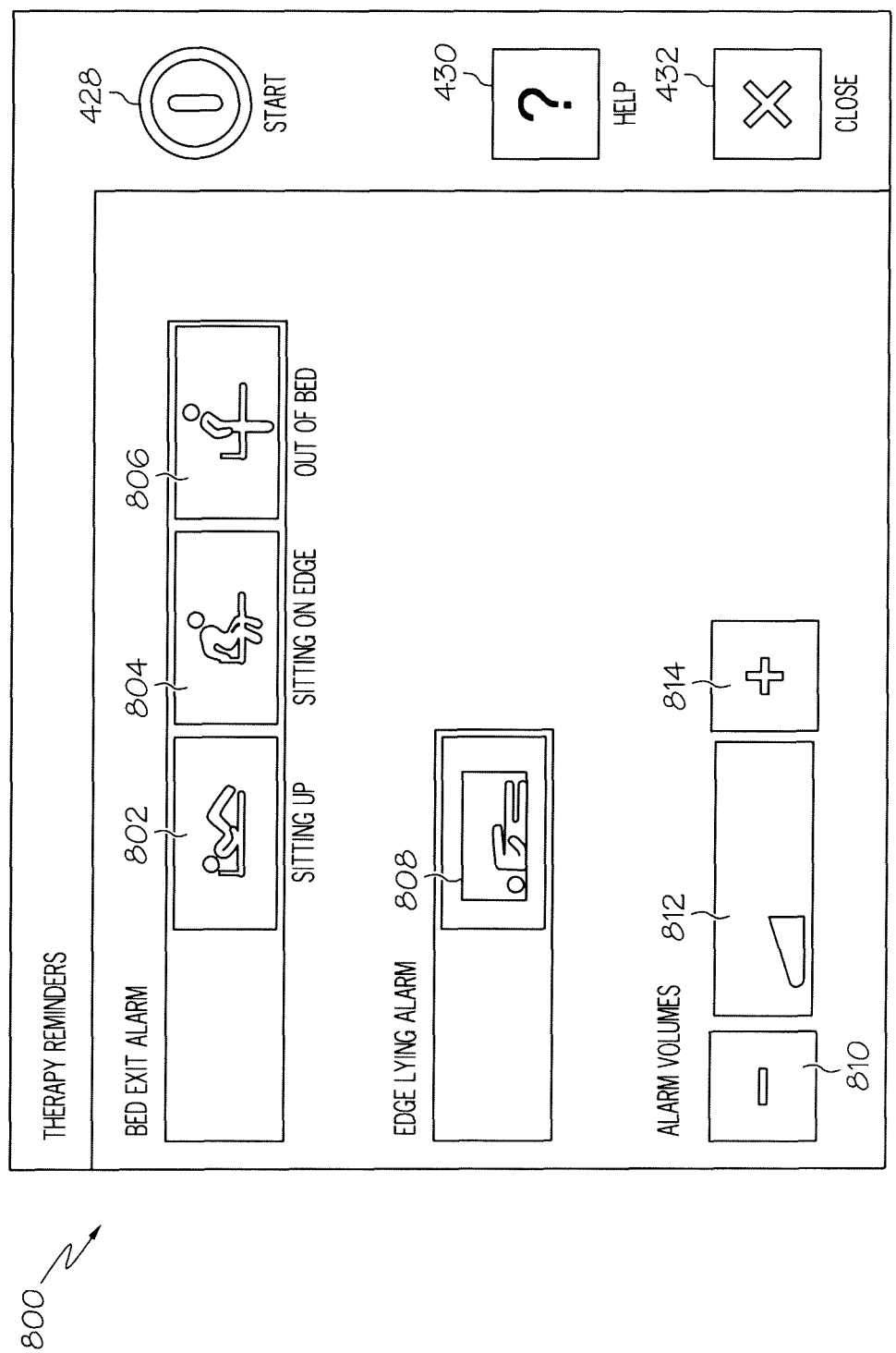

By selecting the alarm selector 328 of FIG. 24, an alarm settings user interface screen 800 as illustrated in FIG. 29 is displayed. Upon selection of this particular interface screen 800, a user can select a bed exit alarm for a sitting up position 802, a sitting on edge of bed position 804, or an out of bed condition 806. For instance, if a patient sits up and the sitting up selector 802 has been selected, whenever a patient sits up an audio or visual alarm will be activated. The volume level of the audio alarm which is activated can be selected by an alarm volume selector 812 which includes a negative or down volume selector 810 and a positive or up volume selector 812. If the bed exit alarm of sitting on edge 804 has been selected, even though a patient sits up in bed, an alarm will not sound. However, when a patient moves to sitting on the edge of the bed, an alarm will sound or otherwise be activated. Should the user select the out of bed condition alarm 806, a patient in a sitting up position or a sitting on edge position will not trigger the alarm. Only when a patient exits the bed will an alarm be activated. An edge lying alarm 808 is also included which indicates to a user that a patient is lying on the bed and is close to an edge which can be a condition that is not desirable.

Figure 30:
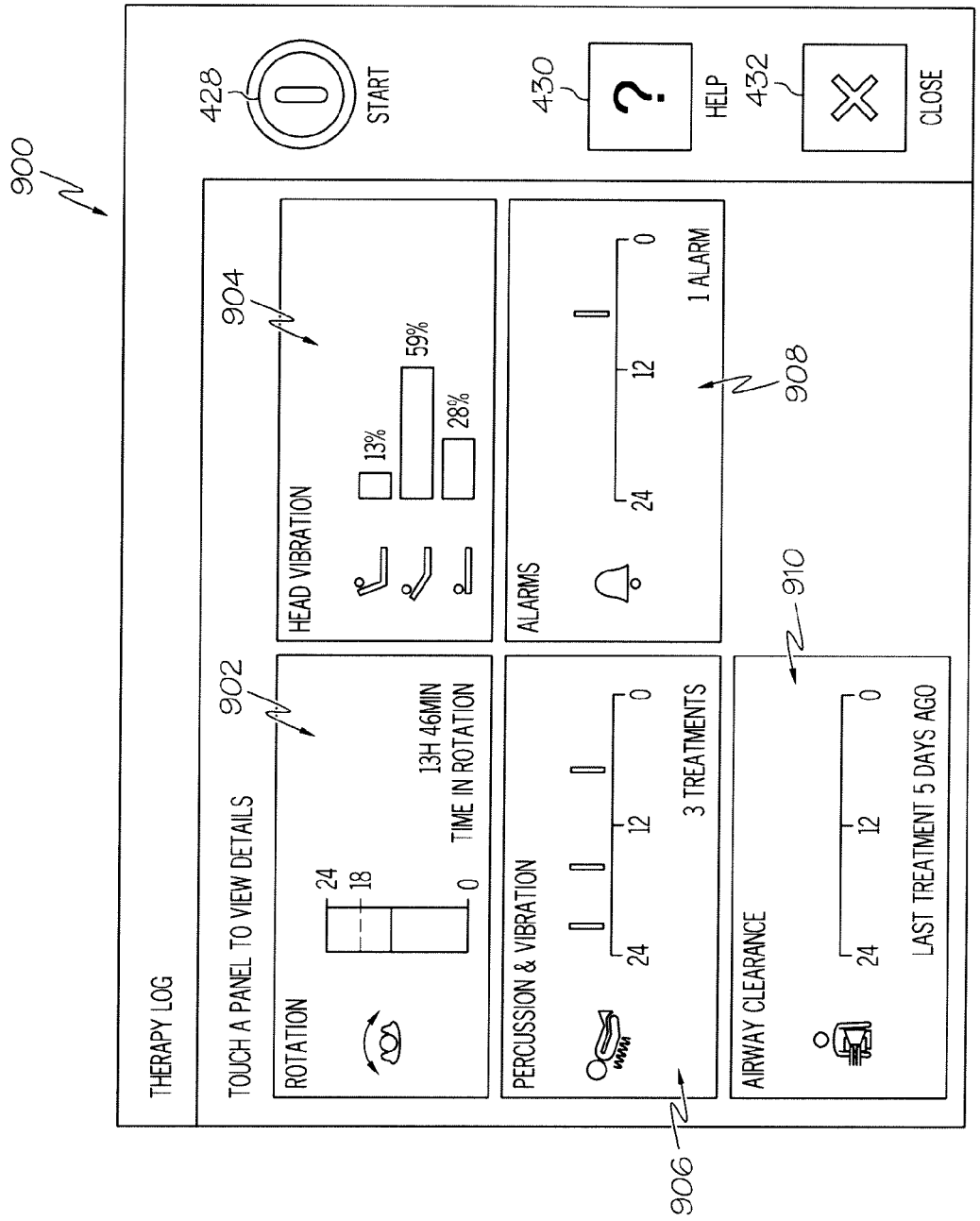

FIG. 30 illustrates a therapy log user interface screen 900 which can be selected by the therapy and controls button 326 of FIG. 24. The therapy log user interface screen 900 can be used to review data which has been stored regarding the various selected therapies over a period of time, for instance, 24 hours as illustrated in FIG. 30. The details of rotation 902, head elevation 904, percussion and vibration 906, alarms activated 908, and airway clearance 910 can be displayed. A visual bar graph of rotation is shown in area 902 as well as the actual hours and minutes of time a patient has experienced rotation. Head elevation is also shown in area 904 as a series of icons which show a horizontal state, a partially elevated state and a more highly elevated state or sitting up state for the patient. Percussion and vibration is illustrated in area 906 by a bar located along a time line of zero to 24 hours to indicate when the percussion and vibration has been applied to a patient. In this instance, three treatments have been applied over a period of 24 hours. In the alarms portion 908 of the user interface screen 900, one alarm occurred over the 24 hour period as shown by the 24 hour time line and as indicated by the statement of one alarm. In the airway clearance portion 910 of the therapy log 900, there have been no treatments over the last 24 hours. However, the portion of the airway clearance area 910 indicates that the last treatment was five days ago. Consequently, if there has been no airway clearance procedures performed over the last 24 hours, the system can display when the last treatment occurred. It is also possible to display similar information for the other four displayed functions. For instance, if there have been no percussion and vibration treatments over the last 24 hours, it is possible to display the number of days which has elapsed since the last treatment.

Although the invention has been described in detail with reference to certain preferred embodiments, variations and modifications exist within the scope and spirit of the present invention. For instance, while the figures illustrate a surface including a plurality of upstanding air cushions having a cylindrical shape, other air cushions are within the scope of the present invention. Air bladder assemblies having horizontally disposed or transversely disclosed bladders are within the scope of the invention. Other pressure or force sensing transducers than those disclosed herein are also within the scope of the present invention. For additional details of such bladders or sensing transducers, please see U.S. Provisional Patent Application Ser. No. 60/821,494, the disclosure of which is incorporated herein by this reference.

What is claimed is:

1. A control unit for a patient support surface configured to provide a plurality of pulmonary therapies, the control unit comprising:
a housing defining an enclosed interior region, the housing spaced from the patient support surface and removably coupled to the patient support surface by a first coupler external to the patient support surface,
a second coupler supported by the housing and configured to operably couple the control unit to an airway clearance system that is external to the patient support surface, and
a controller located within the enclosed interior region of the housing, the controller configured to disable the plurality of pulmonary therapies in response to detecting that the control unit is coupled to the airway clearance system.

2. The control unit of claim 1, wherein the airway clearance system includes a high frequency chest wall oscillation device.

3. The control unit of claim 1, wherein the airway clearance system is wearable by a person when the person is not supported by the patient support surface.

4. The control unit of claim 1, comprising a user interface coupled to the housing by a swivel connector.

5. The control unit of claim 1, comprising a user interface supported by the housing, wherein the user interface is configured to display information relating to the airway clearance system and information relating to the patient support surface.

6. The control unit of claim 1, comprising a holder supported by the housing, wherein the holder is configured to support a deep vein thrombosis (DVT) device.

7. The control unit of claim 1, comprising a user interface supported by the housing, wherein the user interface is configured to display information relating to a pressure relief feature of the patient support surface and settings for a chest wall oscillation device.

8. The control unit of claim 1, comprising a user interface supported by the housing, wherein the user interface supports user controls for the airway clearance system.

9. A control unit for a patient support surface, comprising:
a housing defining an enclosed interior region, the housing spaced from the patient support surface and removably coupled to the patient support surface by a first coupler external to the patient support surface,
a second coupler supported by the housing and configured to operably couple the control unit to an airway clearance system that is external to the patient support surface,
a user interface supported by the housing and configured to selectively activate at least one of a pressure relief mode, a rotation mode, a percussion mode, and a vibration mode of the patient support surface and an airway clearance system mode for the airway clearance system, and
a controller located within the enclosed interior region of the housing and coupled to the user interface, the controller configured to disable the pressure relief mode, the rotation mode, the percussion mode, and the vibration mode in response to detection that the control unit is coupled to the airway clearance system via the second coupler.

10. The control unit of claim 9, wherein the user interface is configured to display an airway clearance screen if the airway clearance mode is selected.

11. The control unit of claim 10, wherein the airway clearance screen comprises user controls for selecting pulse frequency, intensity and time duration parameters for airway clearance therapy.

12. The control unit of claim 9, wherein the user interface comprises a user control to configure an alert relating to airway clearance therapy.

13. The control unit of claim 9, configured to activate airway clearance therapy, monitor airway clearance therapy and generate an alarm relating to airway clearance therapy if an amount of time has elapsed since the last airway clearance therapy.

14. The control unit of claim 9, wherein the user interface is configured to display a history of airway clearance therapy.

* * * * *